(12) United States Patent
Vuran et al.

(10) Patent No.: US 9,532,118 B2
(45) Date of Patent: Dec. 27, 2016

(54) ANTENNA FOR WIRELESS UNDERGROUND COMMUNICATION

(71) Applicant: NUTECH VENTURES, Lincoln, NE (US)

(72) Inventors: Mehmet Vuran, Lincoln, NE (US); Xin Dong, Lincoln, NE (US); David Anthony, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 32 days.

(21) Appl. No.: 14/415,455

(22) PCT Filed: Jul. 18, 2013

(86) PCT No.: PCT/US2013/051102
§ 371 (c)(1),
(2) Date: Jan. 16, 2015

(87) PCT Pub. No.: WO2014/015151
PCT Pub. Date: Jan. 23, 2014

(65) Prior Publication Data
US 2015/0181315 A1  Jun. 25, 2015

Related U.S. Application Data

(60) Provisional application No. 61/673,757, filed on Jul. 20, 2012.

(51) Int. Cl.
*G08C 19/00* (2006.01)
*H04Q 9/14* (2006.01)
(Continued)

(52) U.S. Cl.
CPC ............. *H04Q 9/14* (2013.01); *G01S 13/885* (2013.01); *H01Q 1/04* (2013.01); *H01Q 1/38* (2013.01);
(Continued)

(58) Field of Classification Search
CPC ............. H04Q 9/14; H04L 49/15; H01Q 1/38; H01Q 9/16; H01Q 1/04; G01S 13/885; G01N 33/24
(Continued)

(56) References Cited

U.S. PATENT DOCUMENTS 3,435,457 A * 3/1969 Brueckmann ............ H01Q 1/04
343/719
3,594,798 A * 7/1971 Leydorf .................... H01Q 1/04
343/719
(Continued)

FOREIGN PATENT DOCUMENTS

CN 101167436 A 4/2008
CN 102565150 A 7/2012
(Continued)

OTHER PUBLICATIONS

Silva et al., "Communication with Aboveground Devices in Wireless Underground Sensor Networks: An Empirical Study," IEEE Inernational Conference on Communications. Cape Town: IEEE, May 2010, pp. 1-6 and figure 1.
(Continued)

*Primary Examiner* — Juan A Torres
(74) *Attorney, Agent, or Firm* — Fish & Richardson P.C.

(57) ABSTRACT

Systems and methods are disclosed for an underground antenna structure for radiating through a dissipative medium, the antenna structure. The antenna structure includes a dielectric substrate, a feeding structure disposed on the substrate, and one or more electrical conductors. The one or more electrical conductors are disposed on the substrate, oriented, and buried within the dissipative medium. The electrical conductors are also adapted to radiate signals at a frequency in a half-space adjacent to the dissipative medium. The adaptation include a beamwidth state for one or more of the electrical conductors based at
(Continued)

least in part on the relative permittivity of the dissipative medium.

19 Claims, 16 Drawing Sheets

(51) Int. Cl.
    *G01S 13/88*     (2006.01)
    *H01Q 1/04*     (2006.01)
    *H01Q 9/16*     (2006.01)
    *H01Q 1/38*     (2006.01)
    *H04L 12/933*     (2013.01)
    *G01N 33/24*     (2006.01)

(52) U.S. Cl.
    CPC ................ *H01Q 9/16* (2013.01); *H04L 49/15* (2013.01); *G01N 33/24* (2013.01)

(58) Field of Classification Search
    USPC ...................................................... 340/870.3
    See application file for complete search history.

(56) References Cited

U.S. PATENT DOCUMENTS

| | | | | |
|---|---|---|---|---|
| 3,742,509 A | * | 6/1973 | DeBettencourt | H04B 7/00 343/719 |
| 4,809,010 A | * | 2/1989 | Losee | H01Q 1/04 343/719 |
| 4,829,310 A | * | 5/1989 | Losee | H01Q 1/04 343/719 |
| 4,839,661 A | * | 6/1989 | Losee | H01Q 1/04 343/719 |
| 5,710,568 A | * | 1/1998 | Shirazi | H01Q 1/04 343/700 MS |
| 8,035,403 B1 | | 10/2011 | Campbell et al. | |
| 2012/0019425 A1 | | 1/2012 | Lee et al. | |

FOREIGN PATENT DOCUMENTS

| | | |
|---|---|---|
| CN | 202330229 U | 7/2012 |
| WO | WO 89/12333 | 12/1989 |

OTHER PUBLICATIONS

Silva et al., "Empirical Evaluation of Wireless Underground-to-Underground Communication in Wireless Underground Sensor Networks," Distributed Computing in Sensor Systems. 5th IEEE International Conference DCOSS 2009, Marina del Rey, CA, 2009, vol. 5516, ISBN 978-3-642-02084-1, pp. 234-242 and figure 2.

Australian Office Action in Australian Application No. 2013292513, dated Jul. 22, 2016, 7 pages.

Chinese Office Action in Chinese Application No. 201380043937.0, dated Jul. 11, 2016, 13 pages (with English translation).

Jianting, Research on Wireless Underground Sensor Network, Computer Engineering Application Technology, Jun. 2008, 18: 1738-1740 (with English abstract).

Xiaoya et al., "Channel modeling for wireless underground sensor networks," Annual Computer Software and Applications Conference, Dec. 2011, 249-254.

\* cited by examiner

Mica2 antenna

MicaZ antenna

Circular planar antenna

Elliptical planar antenna

GSM antenna

433 MHz dipole

Circular planar antenna

Elliptical planar antenna

ANTENNA FOR WIRELESS UNDERGROUND COMMUNICATION

CROSS-REFERENCE TO RELATED APPLICATION

This application is a National Stage Application under 35 U.S.C. §371 and claims the benefit of International Application No. PCT/US2013/051102, filed Jul. 18, 2013, which claims priority to U.S. Application Ser. No. 61/673,757, filed on Jul. 20, 2012, entitled ANTENNA FOR WIRELESS UNDERGROUND COMMUNICATION, the disclosure of which is incorporated herein by reference.

FEDERALLY SPONSORED RESEARCH OR DEVELOPMENT

This invention was made with government support under CNS-0953900 awarded by the National Science Foundation. The government has certain rights in the invention.

TECHNICAL FIELD

This disclosure relates to wireless antennas and more particularly to characteristics of an underground antenna for wireless underground sensor networks (WUSNs).

BACKGROUND

Wireless underground sensor networks (WUSNs) are a natural extension of wireless sensor networks (WSNs) to underground settings. WUSNs generally include sensor motes that are buried in soil and can, for example, provide applications in precision agriculture, environment monitoring, and virtual fencing. Establishing wireless communication links in an underground setting can be challenging. Example factors that can add to the challenge include high permittivity of soil, soil-air interface characteristics, and specific real-time soil conditions.

SUMMARY

Systems and methods are disclosed for an underground antenna structure for radiating through a dissipative medium. In addition, systems and methods are disclosed for measuring conditions in a dissipative medium, such as soil. Empirical evaluations are illustrated in FIGS. 3-8 to show that an antenna designed considering both the change in wavelength in soil and the reflection from the soil-air interface can accommodate major changes in soil moisture and improve communication distances by up to 587% compared to antennas that are designed based on only the wavelength change in soil. As an example, selection or design of a particular wide band antenna described in this document can result in an increased communication distance for communications occurring between the antenna and one or more other structures or networks.

In one implementation, an underground antenna structure for radiating through a dissipative medium is disclosed. The antenna structure includes a dielectric substrate, a feeding structure disposed on the substrate, and one or more electrical conductors disposed on the substrate, oriented, and buried within the dissipative medium. In some implementations, the electrical conductors are adapted to radiate signals at a frequency in a half-space adjacent to the dissipative medium. Such an adaptation can, for example, include designing a beamwidth state for one or more of the electrical conductors based at least in part on the relative permittivity (e.g., moisture content) of the dissipative medium. In some implementations, the antenna structure is a wide band antenna that maintains a return loss of less than about minus 10 decibels for a plurality of soil conditions. In one example, the wide band antenna has a diameter of about 100 millimeters and the antenna is buried in non-homogenous soil.

In some implementations, the one or more electrical conductors are oriented toward and substantially parallel to an interface between free space and the dissipative medium and the corresponding radiation pattern emitted by the underground antenna structure is unidirectional towards the interface. In some examples, the antenna structure is buried in the dissipative medium at about 0.1 meters up to about 1.0 meter.

In some implementations, the antenna structure includes circuitry adaptable to provide a beamwidth that accommodates a critical angle of incidence from soil to air at different soil conditions. In some aspects of the antenna structure, the beamwidth state results in a wireless communication distance increase for communications between the underground antenna structure and one or more other structures or networks. The critical angle of incidence may be a critical operating angle θc that is between about 5 degrees and about 15 degrees, in which the critical operating angle θc value is based at least in part on the permittivity of the dissipative medium. In some examples, the critical operating angle θc represents the angle above which no refraction exists for the antenna structure.

In another implementation, a wireless underground system for measuring conditions in a dissipative medium is disclosed. The system includes one or more wireless moisture sensors, each including a sensor board, a processor within the sensor board, and a transceiver in communication with the processor and coupled to an antenna. The system also includes a gateway configured to receive and transmit wireless messages and further configured to communicate with a network and to receive and relay wireless messages from the one or more wireless moisture sensors. In some implementations, each of the wireless moisture sensors are configured to (i) collect data about the conditions of the dissipative medium from the plurality of sensors along a length of the dissipative medium, and (ii) in response to detecting a threshold level of change in the permittivity of the dissipative medium, maintain a threshold level of return loss.

In some implementations, the threshold level of change in the permittivity of the dissipative medium comprises an increase or decrease in the moisture level of the dissipative medium of about 5 percent and the threshold level of return loss is less than about minus 10 decibels.

In some aspects, the one or more wireless moisture sensors can collect data from at least two depths within the dissipative medium. Example depths can include about 0.1 meters below the surface of the dissipative medium (e.g., soil) and about 1.0 meters below the surface of the dissipative medium (e.g., soil)

In another implementation, a method for operating an underground antenna structure radiating through a dissipative medium is disclosed. The method includes measuring, using the underground antenna structure, data associated with the dissipative medium surrounding a plurality of wireless sensors, wherein the plurality of wireless sensors are coupled to the antenna structure. The method also includes maintaining a threshold level of return loss, for the antenna structure, of less than about minus 10 decibels in response to detecting a threshold level of change in the permittivity of the dissipative medium. An example threshold level of change in the permittivity of the dissipative medium may include an increase or decrease in the moisture level of the dissipative medium of about 5 percent. The method also includes transmitting one or more wireless messages from the plurality of wireless sensors using the antenna. The messages may correspond to the measured data.

Advantageously, the described systems and techniques may provide for one or more benefits, such as the increase in information collectable from a wireless underground sensor network based on determining real-time soil characteristics. As another advantage, the use of a wide band antenna in underground communication provides a significant distance increase over antennas that are designed to account for a simple wavelength change in soil.

The details of one or more embodiments are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Antennas used in wireless underground sensor networks (WUSN) can be buried in soil, water, or rock bed. Burying the antennas removes the open air aspect common to antenna wave propagation occurring in traditional communication scenarios. Removal of this open air propagation characteristics generally introduces one or more issues with antenna impedance matching, which in turn, introduces a number of communication issues between one or more antennas in a WUSN.

Wireless communication using electromagnetic signals (i.e., waves) typically involves high levels of signal attenuation when the waves are transmitted through a lossy medium such as soil or rock. In one example, the high level of signal attenuation can be due to absorption of the signal within the medium. The effects can include extreme signal loss, multipath effects due to the inhomogeneous nature of soil, noise due to electrical ground currents, and/or extended black-out periods after a rainfall due to wet soil.

The amount of signal loss when propagating through soil or rock is dependent upon the properties of the material. For example, the existence of excessive water in the soil can produce significant amounts of attenuation which typically increase as the water content of the soil increases. In some implementations, the effect of water on the signal is dependent on the frequency being used in the wireless communication. In general, lower frequencies will experience less attenuation when propagating through the ground. Other soil factors which can affect attenuation of electromagnetic signals propagating through the ground may include, for example, soil density, soil particle size, and/or soil temperature.

Figure 1:
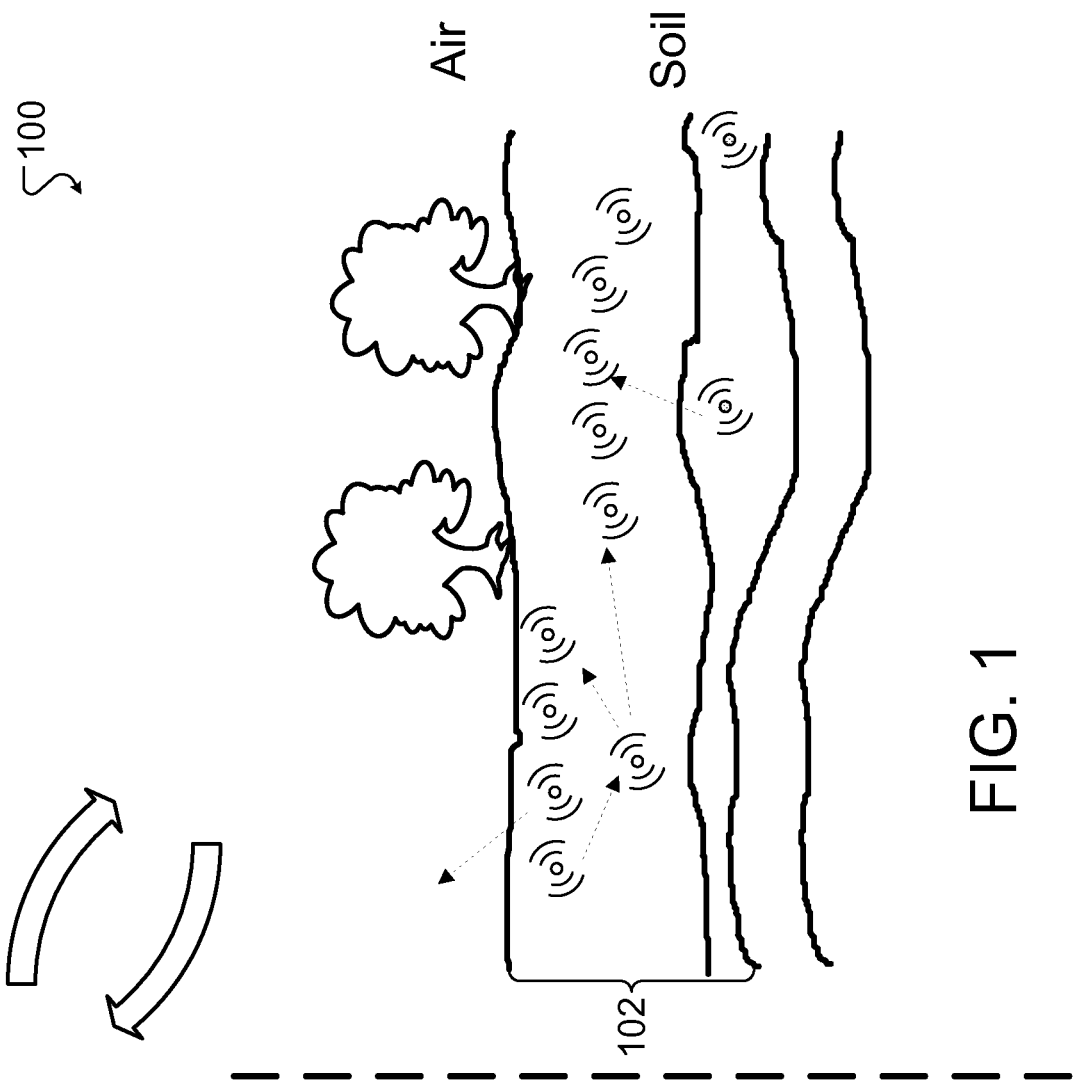
FIG. 1 is a conceptual diagram of a system for measuring soil characteristics and providing underground communication throughout a wireless underground sensor network (WUSN).
Figure 1:
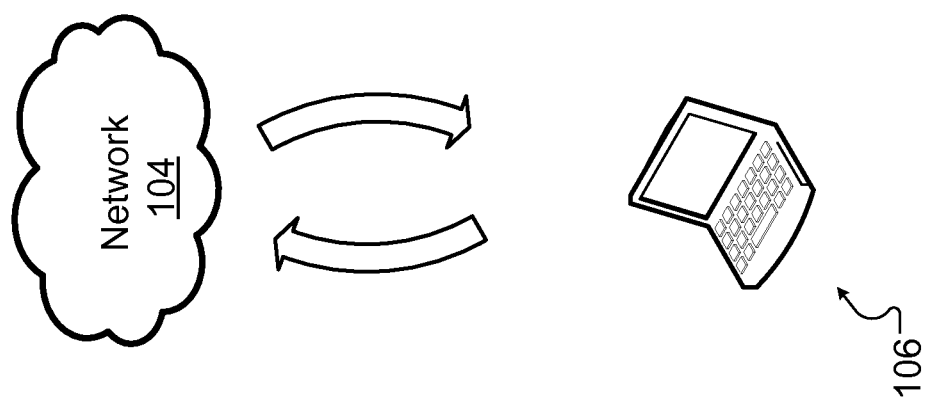

FIG. 1 is a conceptual diagram of a system 100 for measuring soil characteristics and providing underground and aboveground communication throughout a wireless underground sensor network (WUSN) 102. At a high level, system 100 includes a number of sensors in sensor network 102 that are used to measure environmental characteristics. The sensors can represent a wireless communication network in which messages, such as sensor data, operating data, commands, and/or environment data, can be communicated wirelessly between the sensors and one or more networks, such as networks 102 or 104 to reach servers, such as server 106. In some implementations, the server 106 (or other device connected via network 104) can direct information and messages to one or more sensors in the WUSN 102. The communication capabilities for each wireless sensor can depend on a number of environmental factors. Accordingly, circuitry can be designed using antenna design techniques to ensure that changes in soil characteristics and/or environmental factors do not impact the communication capabilities of the sensors.

In general, the sensors in WUSN 102 may be buried in a particular arrangement or spacing. In one example, the sensors can be spaced evenly and buried at the same depth to establish soil measurements in even increments at the same depth. This can, for example, help to understand the irrigation needs for a field of crops. In some implementations, the sensors can be spaced at varying depths and varying spacing based on the particular information desired from the measurements. Each sensor can include a sensor board, a processor within the sensor board, and a transceiver in communication with the processor and coupled to an antenna.

In some implementations, the sensors may be wireless moisture sensors that are configured to collect data about the conditions of a dissipative medium (e.g., soil). For example, the sensors can detect changes in the soil, such as a threshold level of change in the moisture of the soil.

The sensors can be connected via a wireless gateway configured to receive and transmit wireless messages. The gateway may also be configured to communicate with one or more networks and to receive and relay wireless messages from the plurality of wireless moisture sensors.

In underground communications, there are a number of factors that can be used to determine the impedance of the antenna. Such factors can include, but are not limited to, the wavelength in soil, the reflection from the soil-air interface, and the change in soil moisture. In the following examples, antennas can be represented as $Z_a$ and transceivers may be represented as $Z_s$. For efficient wireless communication, the impedance of an example antenna $Z_a$ is typically matched to the output impedance of an example transceiver $Z_s$ such that the radiated power is maximized and the returned power to the transmitter is minimized.

In operation, the impedance of an underground antenna $Z_a^u$ is a function of wavelength, which is shortened when electromagnetic waves propagate in soil. Thus, for a given frequency, a matched antenna in air will likely not be matched when buried in soil. In addition, underground antennas used in WUSN applications for agriculture typically include a number of sensor motes, each with one or more antennas (e.g., one or more antennas and/or antenna arrays). These sensor motes are typically buried at depths from (0.3-1) meters. At this burial depth, reflections from the soil-air interface may disturb current distribution on the antenna, which can further change the ideal impedance of the antenna. Thus, the soil cannot be considered as an infinite medium. As such, the examples and techniques described in this specification employ a half-space model. Consequently, an antenna, which is matched in a homogeneous soil medium, may not be matched in this half-space situation. Another unique characteristic of soil is that its permittivity changes with the variation of the soil moisture. Thus, an underground antenna may be designed to accommodate the impedance changes caused by the variation of the soil moisture over the lifetime of the WUSN. Examples of impedance matching, soil permittivity analysis, buried antenna simulations, and antenna design to accommodate soil characteristics, are described below.

The use of a half-space model, as used in this document, includes two media (e.g., soil and air) divided by a plane.

Relative Permittivity of Soil

When an electromagnetic wave is incident into soil, the wavelength changes because of the higher permittivity of soil compared to that of air. Soil permittivity depends on a number of soil properties, such as bulk density, soil texture, soil moisture (Volumetric Water Content), salinity, and temperature, just to name a few examples. Several models can be used to capture the characteristics of the relative permittivity. These models describe the relative permittivity of different components of soil-water mixture, namely, soil, air, free water, and bounded water. In the following example, a semi-empirical permittivity model for soil is used, but other models can be substituted. Accordingly, the effective permittivity of soil-water mixture, which is a complex number, can be modeled as:

$$\epsilon_s = \epsilon_s' - \epsilon_s'' \tag{1}$$

$$\epsilon_s' = \begin{cases} \left[1.15\left[1 + \frac{\rho_b}{\rho_s(\epsilon_s^\delta - 1)} + (m_v)^{v'}(\epsilon_{f\omega}')^\delta - m_v\right]^{\frac{1}{\delta}} - 0.68 \\ \quad 0.3 \text{ GHz} \le f \le 1.4 \text{ GHz} \\ \left[1 + \frac{\rho_b}{\rho_s(\epsilon_s^\delta - 1)} + (m_v)^{v'}(\epsilon_{f\omega}')^\delta - m_v\right]^{\frac{1}{\delta}} \\ \quad 1.4 \text{ GHz} \le f \le 18 \text{ GHz} \end{cases} \tag{2}$$

$$\epsilon_s'' = \left[(m_v)^{v''}(\epsilon_{f\omega}'')^\delta\right]^{1/\delta} \tag{3}$$

where f is the frequency in Hertz, $\epsilon_s$ is the relative complex dielectric constant of the soil-water mixture, $m_v$ is the volumetric water content, $\rho_b$ is the bulk density, and $\rho_s$ is the particle density, and $\delta$, v', and v'' are empirically determined soil-type dependent constants given by:

$$\delta = 0.65 \tag{4}$$

$$v' = 1.2748 - 0.519S - 0.152C \tag{5}$$

$$v'' = 1.33797 - 0.603S - 0.166C \tag{6}$$

where S and C represent the mass fractions of sand and clay, respectively. The quantities, $\epsilon'_{f\omega}$ and $\epsilon''_{f\omega}$ in equations (2) and (3), represent the real and imaginary parts of the relative permittivity of free water, and are calculated form the Debye model to obtain:

$$\epsilon'_{f\omega} = e_{\omega\infty} + \frac{\epsilon_{\omega 0} - \epsilon_{\omega\infty}}{1 + (2\pi f \tau_\omega)^2} \tag{7}$$

$$\epsilon''_{f\omega} = 2\pi f \tau_\omega \frac{\epsilon_{\omega 0} - \epsilon_{\omega\infty}}{1 + (2\pi f \tau_\omega)^2} + \frac{\delta_{eff}(\rho_s - \rho_b)}{2\pi \epsilon_0 f \rho_s m_v} \tag{8}$$

where $\epsilon_{\omega\infty} = 4.9$ is the limit of $\epsilon'_{f\omega}$ when $f \to \infty$, $\epsilon_{\omega 0}$ is the static dielectric constant for water, and $\epsilon_0$ is the permittivity of free space. Expressions for $\tau_\omega$ and $\epsilon_{\omega 0}$ are given as a function of temperature. At room temperature (20 degrees Celsius), $2\pi\tau_\omega = 0.58 \times 10^{-10}$ s and $\epsilon_{\omega 0} = 80.1$. The effective conductivity $\delta_{eff}$ in (8), in terms of the textural properties of the soil, is given by:

$$\delta_{eff} = \begin{cases} 0.0467 + 0.2204\rho_b - 0.4111S + 0.6614C \\ \quad 0.3 \text{ GHz} \le f \le 1.4 \text{ GHz} \\ -1.645 + 1.939\rho_b - 2.2562S + 1.594C \\ \quad 1.4 \text{ GHz} \le f \le 18 \text{ GHz} \end{cases} \tag{9}$$

Impedance of a Dipole Antenna in Homogeneous Soil

To model the impedance and return loss of a buried antenna, we first consider the antenna in a homogeneous soil. In such an example setting, the impacts of the soil properties on the impedance can be captured. The results calculated in this example can be used as a basis for analyzing a realistic soil environment where an antenna is buried close to the surface.

Due to the high permittivity of soil, $\epsilon_s$, the wave number and hence, the wavelength in soil are not the same as in air. By employing the semi-empirical model of soil permittivity, the wave number for soil $k_s$ can be calculated as:

$$k_s = \beta - i\alpha = 2\pi f \sqrt{\mu_0 \epsilon_s \epsilon_0} \tag{10}$$

where f represents the frequency of the wave, $\mu_0$ and $\epsilon_0$ are the permeability and permittivity in air, respectively, and $\epsilon_s$ represents the relative permittivity of soil defined in equation (1). Then, the ratio of the wavelength in soil, $\lambda_s$, and the wavelength in air $\lambda_0$ is:

$$R_\lambda = \frac{\lambda_s}{\lambda_0} = Re\left\{\sqrt{\frac{1}{\epsilon_s}}\right\} \tag{11}$$

It is shown in equations (10) and (11) that due to the relative permittivity of soil, $\epsilon_s$, wavelength in soil is not the same as in air for a given frequency f. Conversely, for an antenna designed for a specific wavelength, the resonant frequency in soil is not the same as the resonant frequency in air. Moreover, the relative permittivity of the soil changes because of volumetric water content $m_v$, which changes the wavelength of an electromagnetic wave.

Closed form representation of the impedance of an arbitrary antenna is not easily obtained and as such, approximations for the impedance of a dipole antenna are provided in the examples below. Analysis of other types of antennas will be described in reference to FIGS. 5A-5F below.

By employing the induce-emf method, the input impedance of a dipole less than a half of a wavelength long can be approximated as:

$$Z_0 \approx f_1(\beta l) - i\left(120\left(\ln\frac{2l}{d} - 1\right)\cot(\beta l) - f_2(\beta l)\right) \quad (12)$$

where $$f_1(\beta l) = -0.4787 + 7.3246\beta l + 0.3963(\beta l)^2 + 15.6131(\beta l)^3 \quad (13)$$

$$f_2(\beta l) = -0.4456 + 17.0082\beta l - 8.6793(\beta l)^2 + 9.6031(\beta l)^3 \quad (14)$$

$\beta$ represents the real part of the wave number in equation (10), d represents the diameter of the dipole, and l represents half of the length of the dipole. Employing equations (10) and (11) $\beta l$ is represented as:

$$\beta l = \frac{2\pi l}{\text{Re}\left\{\frac{1}{\in_s}\right\}\lambda_0} \quad (15)$$

Since the permittivity of soil $\in_s$ is frequency dependent, $\beta l$ is not a linear function of $1/\lambda_0$. As such, when the antenna is moved from air to soil the resonant frequency changes according to equations (10) and (11) and the antenna impedance value at the resonant frequency also varies with the soil properties.

Impedance of a Buried Antenna in Half Space

Figure 2A:
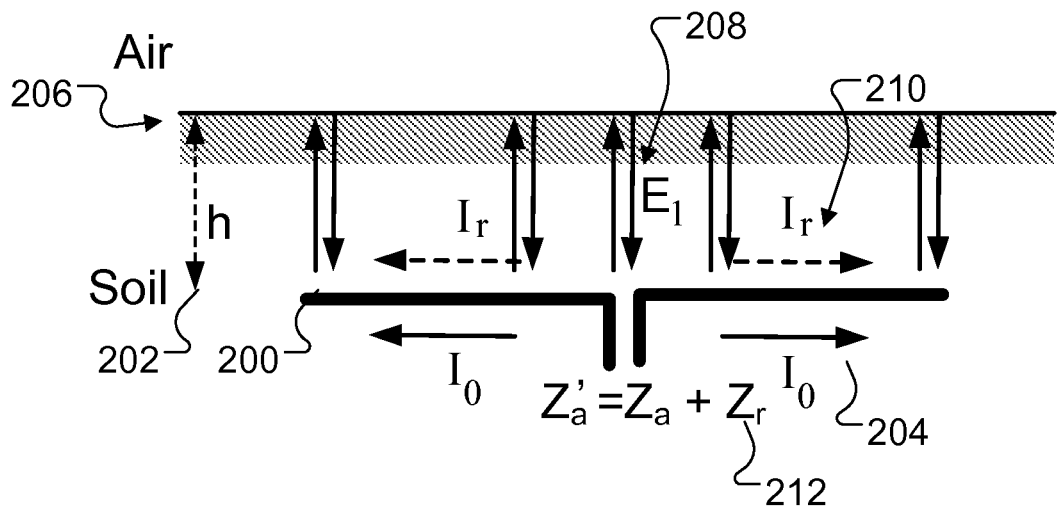
FIGS. 2A-2B are conceptual diagrams showing an example analysis of underground antennas.
Figure 2B:
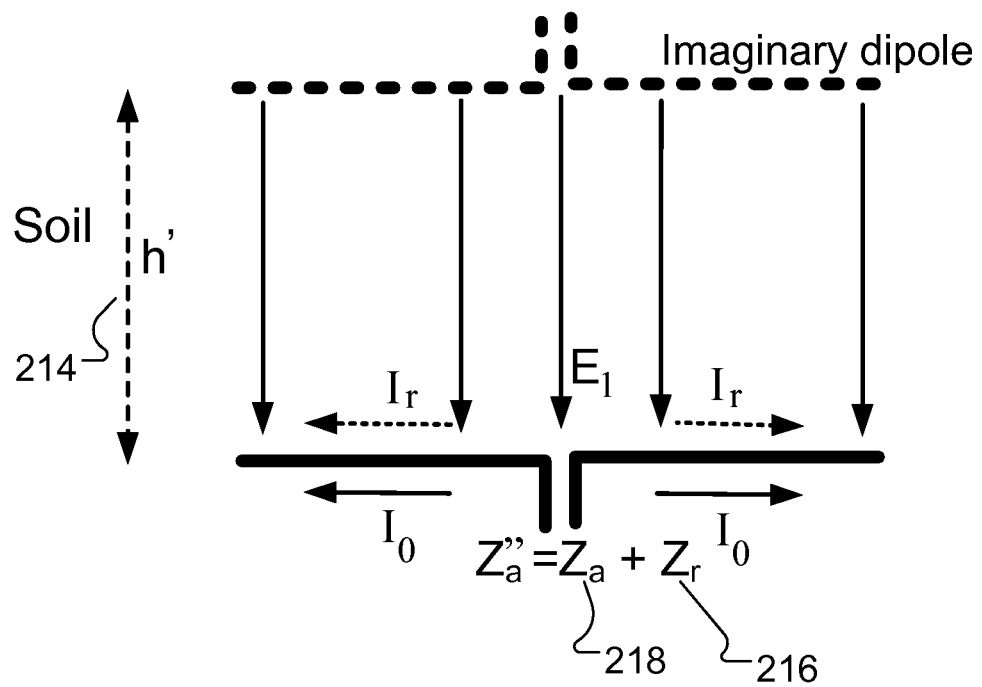

FIGS. 2A-2B are conceptual diagrams showing an example analysis of an underground antenna 200. The analysis above captures the impacts of soil properties. In a real deployment for WUSNs, however, sensor motes are buried at subsurface depths (0.3-1.0) meters as shown by (h) 202 in FIG. 2A. At these depths, the environment cannot be modeled as homogeneous soil due to the impacts of soil-air interface. Instead, the environment can be modeled as a half-space to capture the impacts of the reflected waves from the soil-air interface on the impedance and return loss of the antenna.

As shown in FIG. 2A, when the buried antenna 200 is excited, a current distribution of $I_0(\zeta)$ 204 is generated along the antenna 200. The generated wave propagates towards the soil-air interface 206, where it is reflected and refracted. The reflected electric field that reaches the antenna is denoted as $E_r$ 208, which, in turn, induces a current $I_r$ 210 on the antenna. In some implementations, the current further impacts the generated wave and higher order reflection effects exist. However, due to the high attenuation in soil, these higher order effects are negligible and as such, the following calculations consider only the first order effects.

The induced current on the dipole $I_r$ 210, as well as the resulting impedance $Z_r$ 212, can be modeled as the result of a field generated by an imaginary dipole placed in a homogenous soil environment, as shown in FIG. 2B. The distance of the two dipoles h' 214 is chosen such that $E_r$ 208 is the same at the real dipole as in FIG. 2A. Accordingly, $Z_r$ 216 is modeled based on a modified mutual impedance model between two dipole antennas. The mutual impedance $Z_r$ 216 is then added to itself impedance $Z_a$ 218, as shown by equation (12) to obtain a total impedance of the buried antenna in half space. To calculate $Z_r$ 216, the current distribution on the antenna and the electric field, $E_r$ 208, are modeled first. The current distribution on a short dipole in homogeneous soil can then be approximated as:

$$I_0\zeta = I_m \sin[k_s(l - |\zeta|)] \quad (16)$$

where $I_m$ represents the amplitude of the current and $k_s$ represents the wave number in soil given in equation (10). Based on this current distribution, the reflected $E_r$ field from the soil-air interface at the antenna is:

$$E_r = -i30I_m\left[\frac{e^{-ik_s r_1}}{r_1} + \frac{e^{-ik_s r_2}}{r_2} - 2\cos k_s l \frac{e^{-ik_s r}}{r}\right] \times \Gamma \quad (17)$$

where $$r = [(2h)^2 + \zeta^2]^{1/2} \quad (18)$$

$$r_1 = [(2h)^2 + (\zeta - 1)^2]^{1/2} \quad (19)$$

$$r_2 = [(2h)^2 + (\zeta + 1)^2]^{1/2} \quad (20)$$

and h is the burial depth of the antenna, and $\Gamma$ is the reflection coefficient at the soil-air interface, which is given by:

$$\Gamma = \frac{1}{1 + k_0/k_s} - 1 = \frac{2}{1 + \sqrt{\frac{1}{\in_s}}} - 1 \quad (21)$$

where $k_0$ is the wave number in air.

Considering the imaginary dipole is identical to the dipole in soil, mutual impedance model can be simplified as:

$$Z_r = -\frac{1}{I_m \sin^2(k_s l)} \int_{-1}^{1} E_r(\zeta) \sin k_s(l - |\zeta|) d\zeta \quad (22)$$

Thus, the total impedance of the antenna is $Z_a^u = Z_a + Z_r$ and accordingly, the return loss of the antenna (in dB) is given by:

$$RL_{dB} = 20\log_{10}\left|\frac{Z_s + Z_a^u}{Z_s - Z_a^u}\right| \quad (23)$$

Figure 3A:
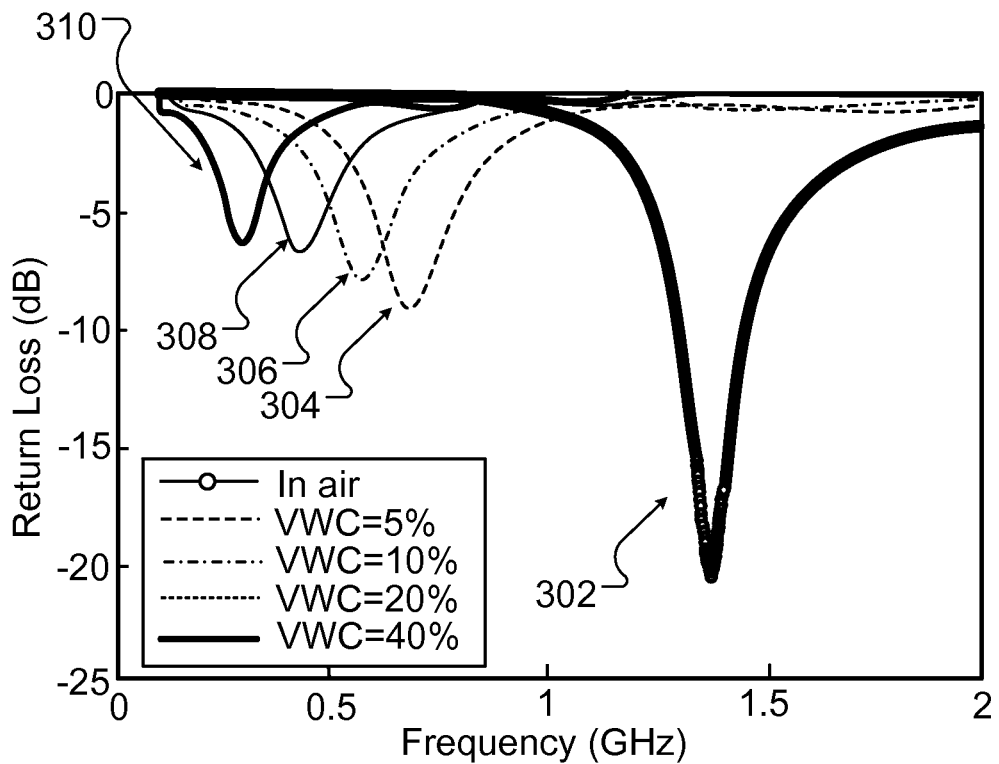
FIGS. 3A-3C illustrate an example theoretical analysis of return loss of a dipole antenna in air and soil.
Figure 3B:
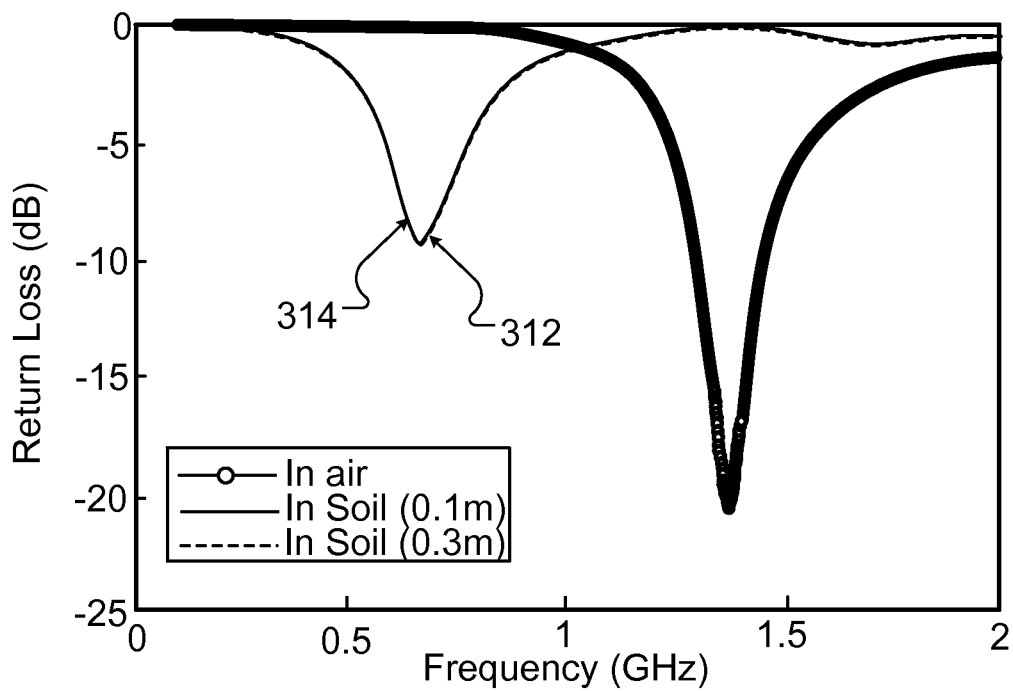
Figure 3C:
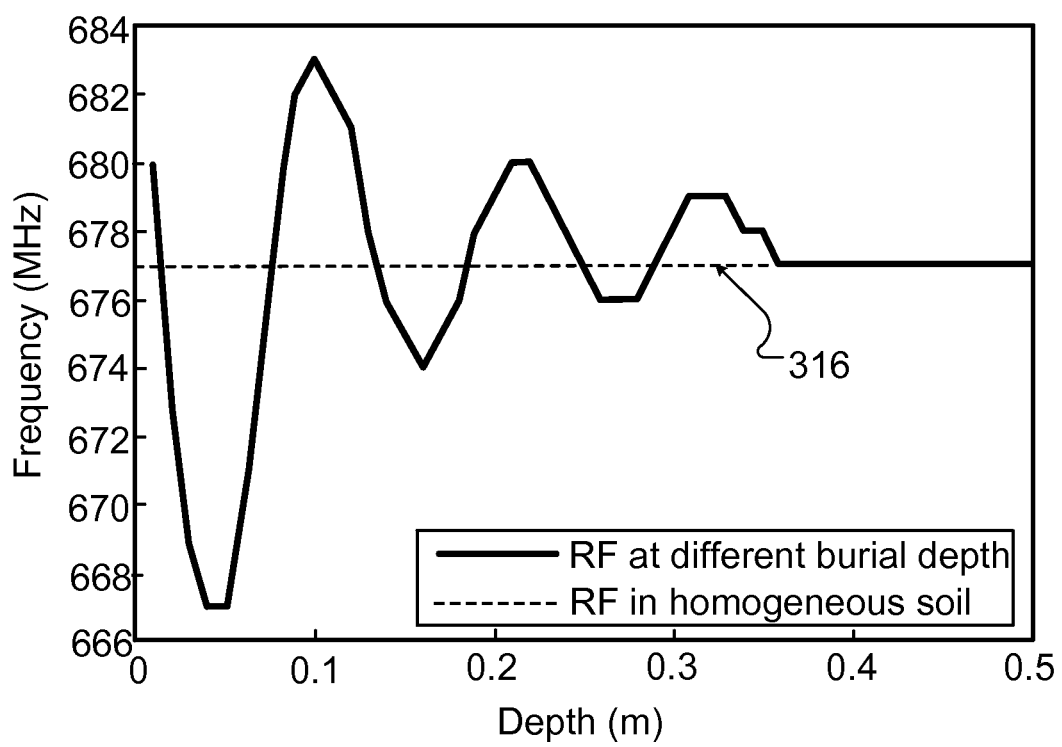

By employing this model, the return loss of an antenna of 50 millimeters (mm) long and 2 mm in diameter can be calculated for air and soil. The calculated results are shown in FIGS. 3A-3B, where the return loss of the dipole is shown for the frequency range of 100 MHz to 2 GHz. FIGS. 3A-3C illustrate an example theoretical analysis of return loss of a dipole antenna in air and soil. In these examples, the resonant frequency of the antenna shifts from 1.382 GHz in air to lower frequency values when the antenna is buried. The shift is due to the shorter wavelength in soil. In FIG. 3A, the antenna is buried at 0.1 m and four different volumetric water content values are analyzed. Namely, volumetric water content values are measured in air 302, at 5% 304, at 10% 306, at 20% 308, and at 40% 310. As shown, the volumetric water content values have a strong impact on the value of the resonant frequency. An increase in volumetric water content from 5% to 40% results in a decrease in the resonant frequency from 685 MHz to 287 MHz.

As shown in FIG. 3B, two different burial depths of 0.1 meters and 0.3 meters are considered. The resonant frequency decreases from 685 MHz 312 to 674 MHz 314 when the burial depth is increased from 0.1 meters to 0.3 meters. The change in the resonant frequency as a function of burial depth is shown in FIG. 3C. As shown, the resonant frequency fluctuates over different burial depths. This is typically caused by the phases of the reflected wave. When the burial depth increases, the impact of the reflected wave decreases as it is attenuated and the resonant frequency converges to that in homogenous soil. The resonant frequency, shown here by arrow 316, is 677 MHz.

Figure 4A:
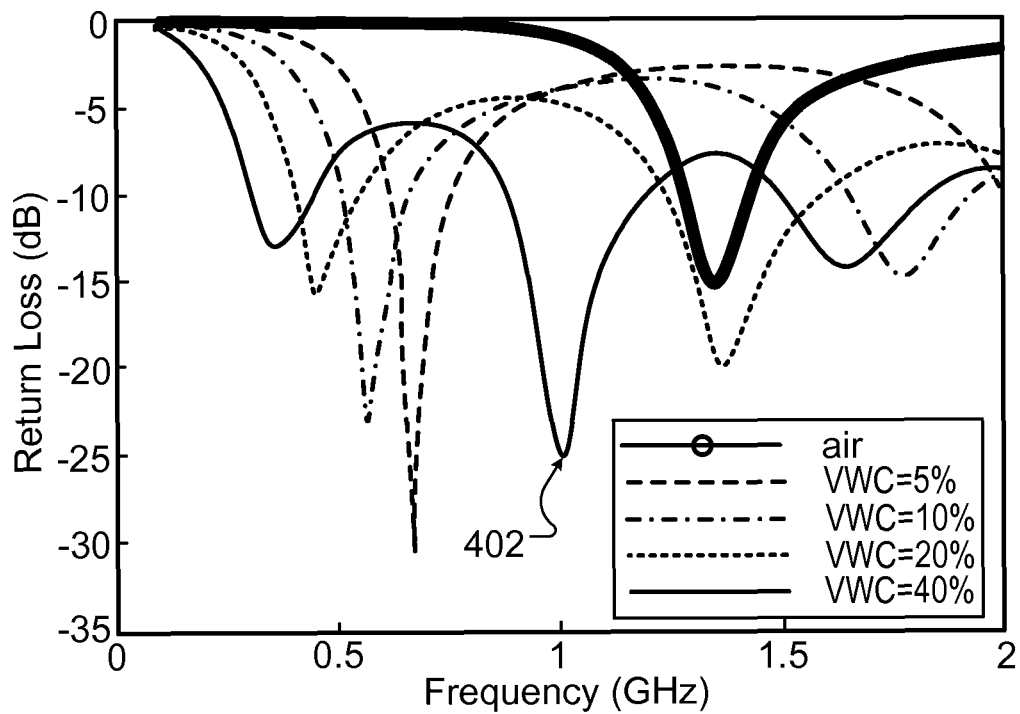
FIGS. 4A-4B illustrate an example simulation of a dipole antenna in air and soil.
Figure 4B:
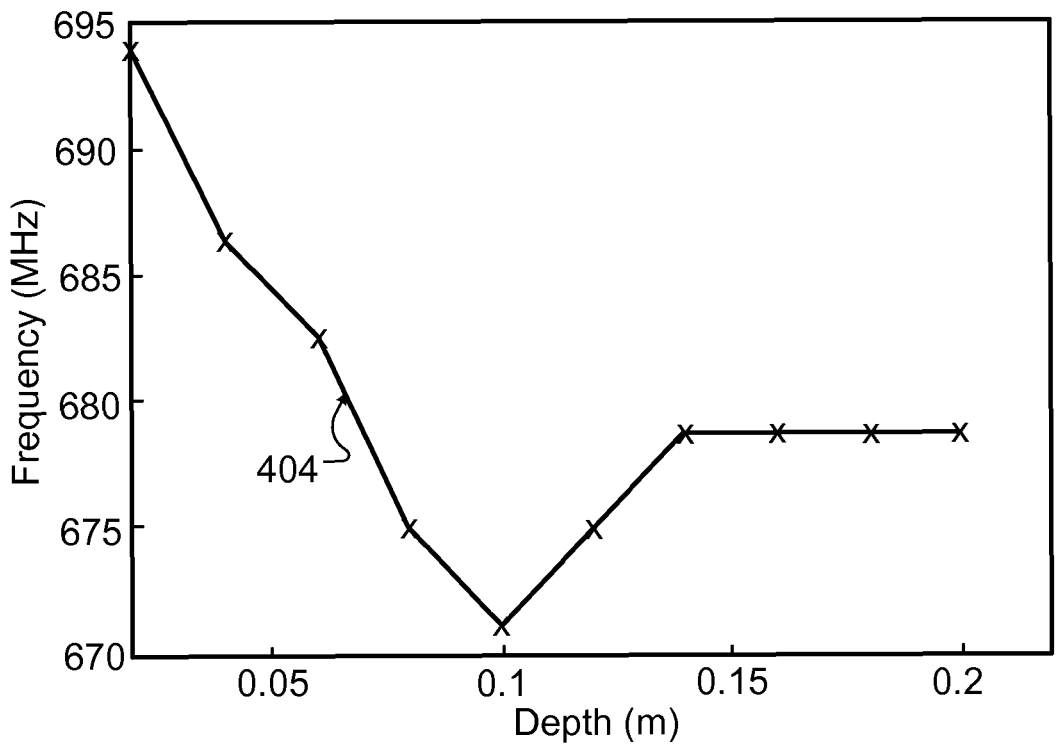

FIGS. 4A-4B illustrate an example simulation of a dipole antenna in air and soil. The simulations described in this example were performed in a high frequency structure simulator (HFSS). The dimensions of the antenna are kept the same as in the examples described in FIGS. 3A-3C above.

To capture the properties of the soil environment, a soil material is created in the HFSS based on the relative permittivity calculated by the model in the example described in FIGS. 3A-3C. In addition, since the relative permittivity of soil is frequency dependent, in this simulation, it is represented according to equation (1).

As shown in FIG. 4A, the return loss of a dipole antenna is shown for a number of different soil moisture values. In this example, the burial depth of the antenna is 0.1 meters. As indicated in the theoretical analysis of FIGS. 3A-3C, the resonant frequency moves to lower frequency ranges when the soil moisture increases.

In this example, the absolute values of the return loss at the resonant frequencies are notably different between example 3A and 4A. This is because of the inaccuracies in modeling an "ideal" antenna in HFSS as well as limitations of the theory due to approximations that are made for tractability. For example, at a volumetric water content of 40%, an additional resonant frequency 402 at 1 GHz is observed that is not shown in FIG. 3A. At this soil moisture level and frequency, the wavelength is smaller than the antenna size, whereas the approximation in equation (12) is typically valid for wavelength values higher than twice the dipole length.

As shown in FIG. 4B, the resonant frequency 404 at different burial depths is depicted from zero to 0.2 meters. The effect of the reflected wave changes the impedance and the resonant frequency. Compared to the theoretical analysis in FIGS. 3A-3C above, the result from HFSS shows less frequency fluctuation and converges to the resonant frequency in homogenous soil more quickly. In both cases, the effects of the soil-air interface are visible in underground antenna design.

It is shown in both examples in FIGS. 3A-3C and FIGS. 4A-B that the design of an antenna for underground communication is influence mainly by three factors: the wavelength in soil, the reflection from the soil-air interface, and the soil moisture. However, the theoretical analysis in FIGS. 3A-3C applies to a dipole only, and as such, other types of antennas cannot be captured using such a method. Thus, field tests are described in the following sections.

Underground Antenna Examples

To further investigate the effects of the soil-air interface on the return loss of antennas and obtain insight into the design of antennas for underground communication, empirical experiments are described below.

Figure 5A:
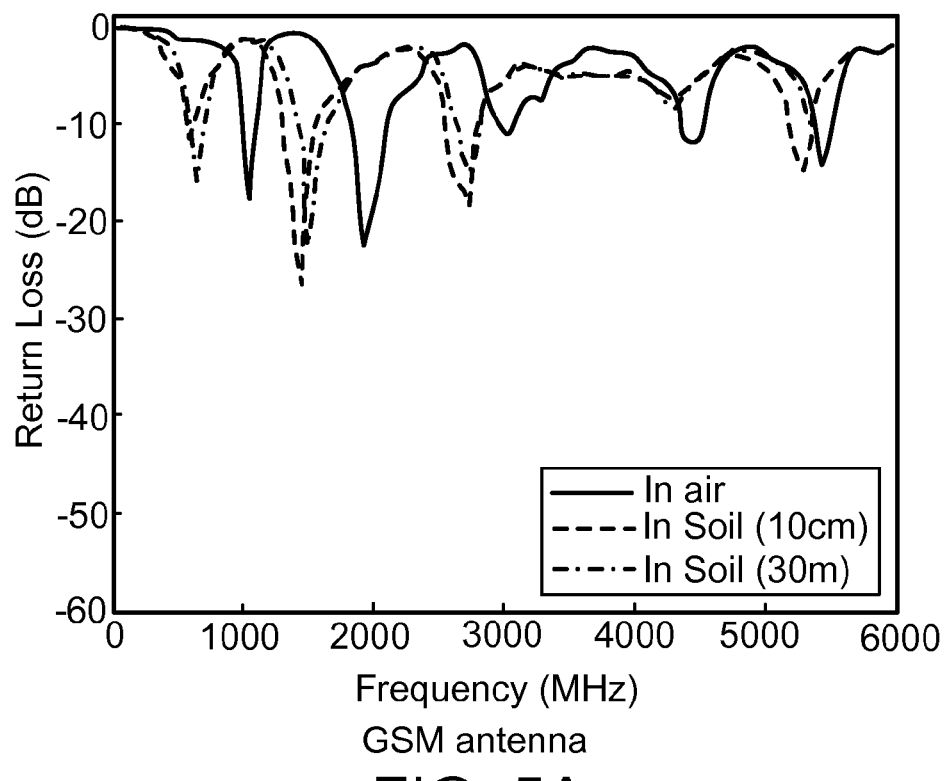
FIGS. 5A-5F illustrate measured return losses for different antenna types.
Figure 5B:
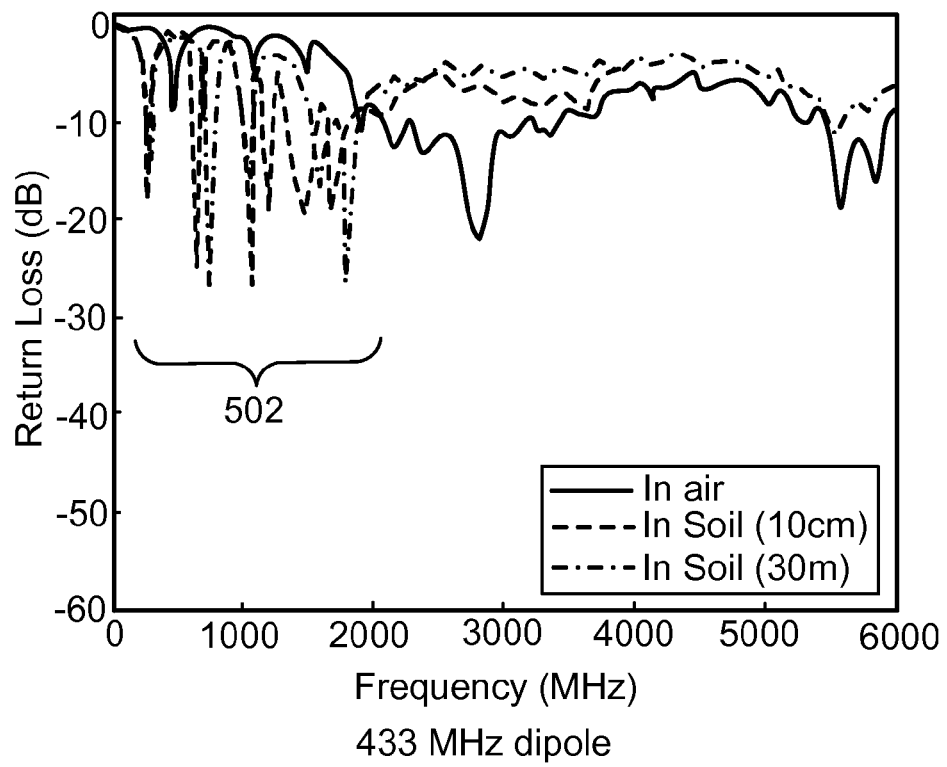
Figure 5C:
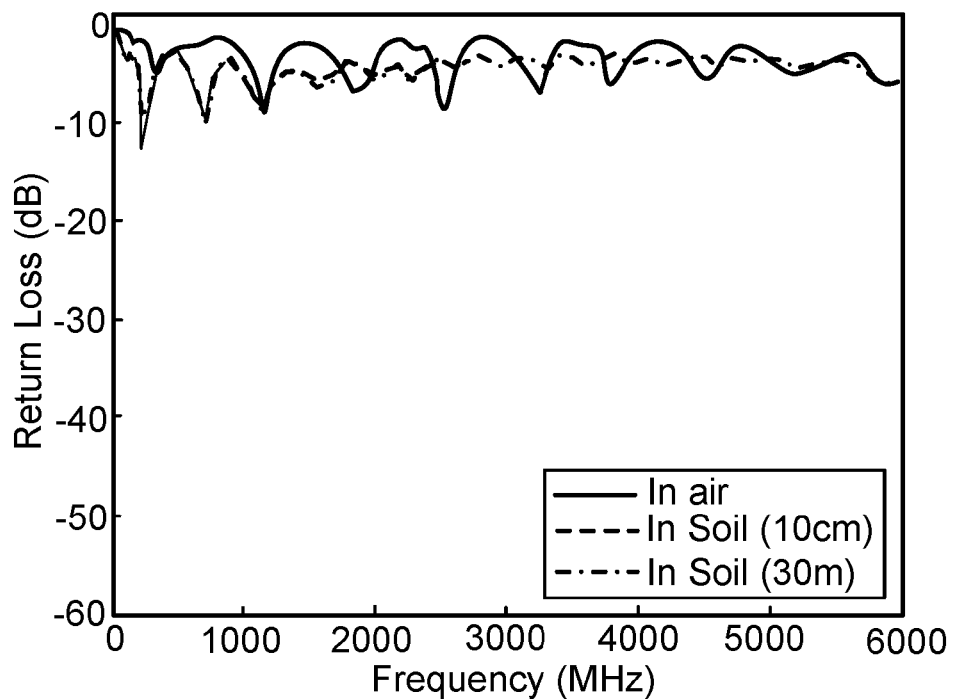
Figure 5D:
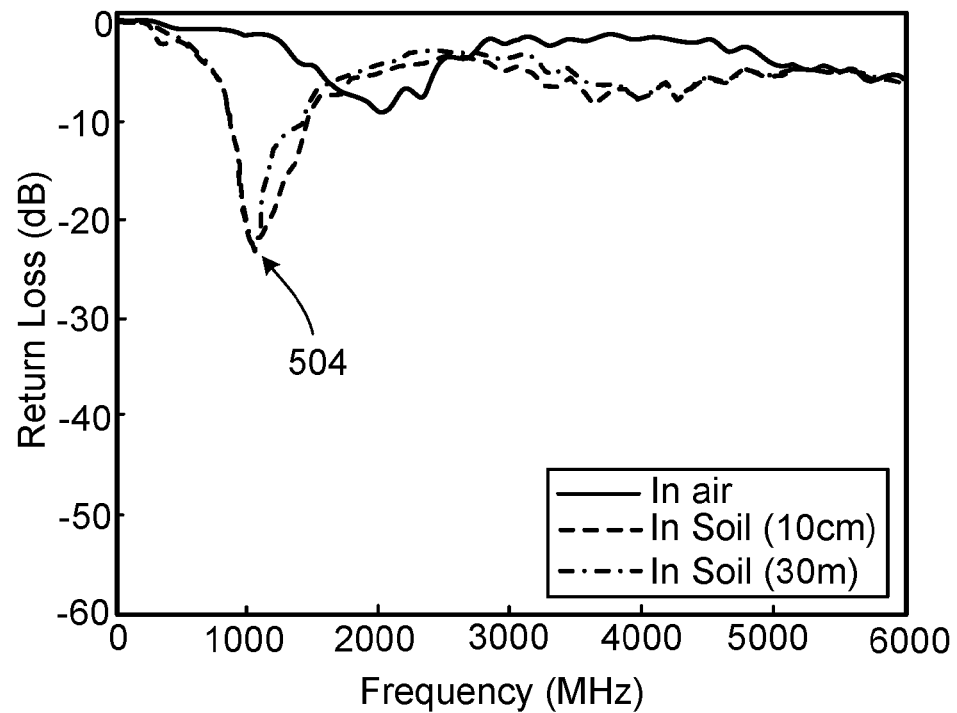
Figure 5E:
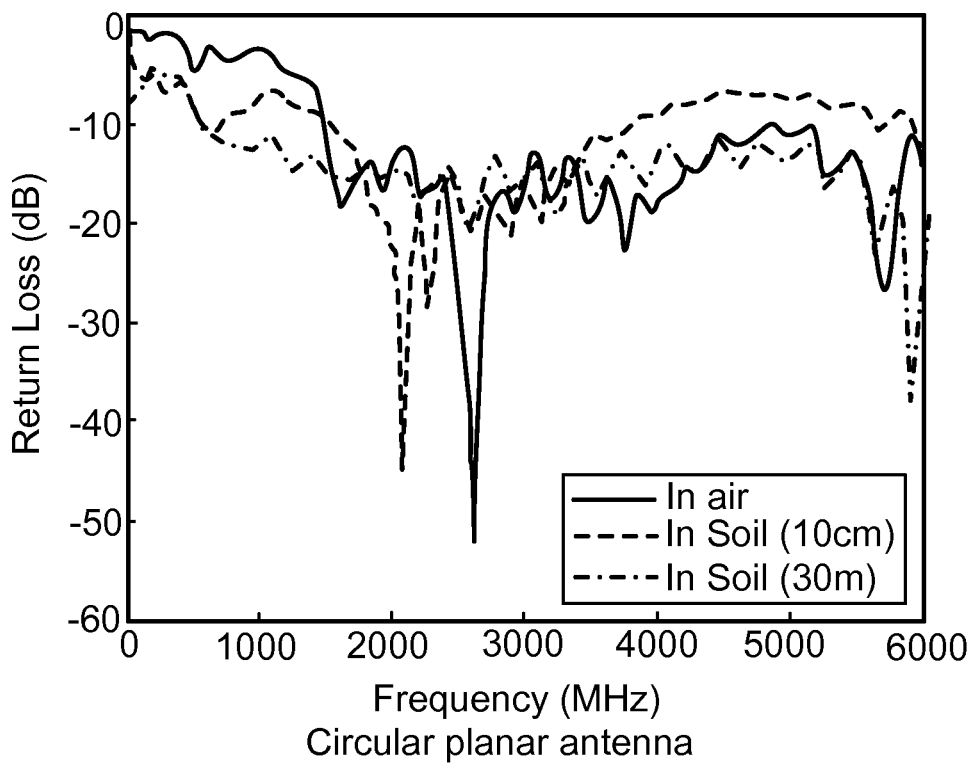
Figure 5F:
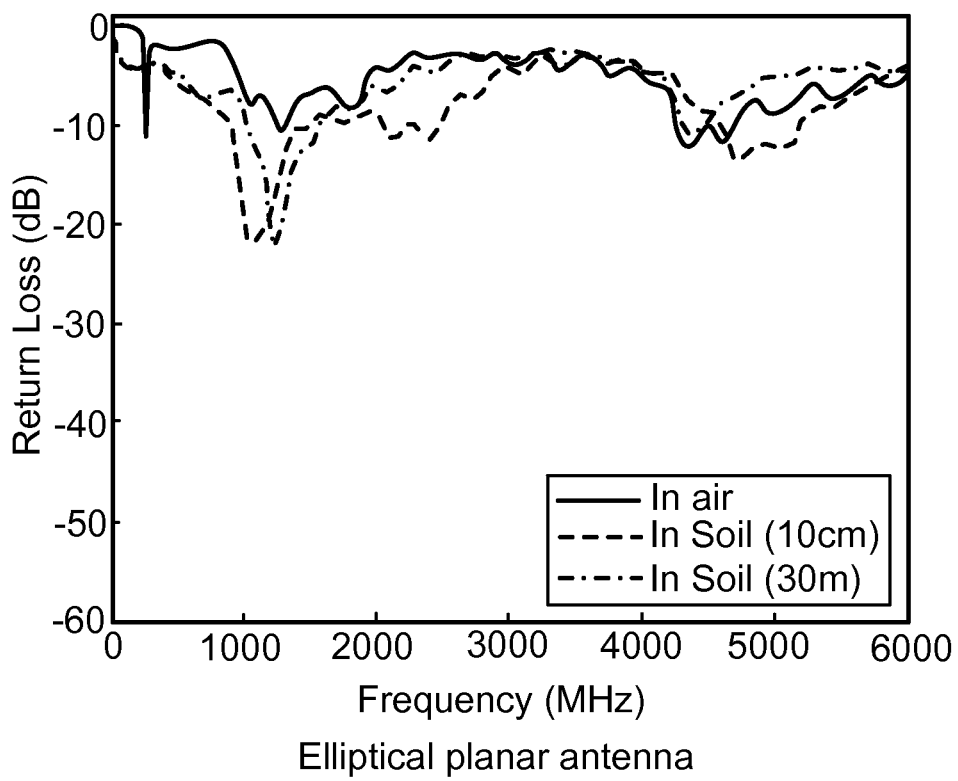

FIGS. 5A-5F illustrate measured return losses for different antenna types. The different antenna types include four dipole antennas and two planar antennas. In particular, the antennas include a GSM antenna (FIG. 5A), a 433 MHz dipole antenna (FIG. 5B), a Mica2 antenna (FIG. 5C) [available from Crossbow Technology, Inc., San Jose, Calif.], a MicaZ antenna (FIG. 5D) [available from Crossbow Technology, Inc., San Jose, Calif.], a circular planar antenna (FIG. 5E), and an elliptical antenna (FIG. 5F).

The GSM antenna (FIG. 5A) is a dipole antenna designed for GSM devices. It is 50 mm long and is isolated by rubber. The radius of the antenna with the isolator is 4 mm. The resonant frequencies are 900 MHz and 1900 MHz.

The 433 MHz dipole antenna (FIG. 5B) is an off-the-shelf antenna designed for the 433 MHz frequency. It is 70 mm long and is also isolated. The radius of the isolator is 5 mm.

The Mica2 antenna (FIG. 5C) is originally attached to the Mica2 motes that are frequently used in wireless sensor network (WSN) experiments. It is a whip antenna of 180 mm long. The antenna is very thin. Including the isolator, the radius is 1.5 mm and the resonant frequency is 433 MHz.

The MicaZ antenna (FIG. 5D) is originally attached to the MicaZ motes. Since MicaZ works at higher frequency (e.g., 2.4 GHz), the antenna is shorter at a length of 37 mm.

The circular planar antenna (FIG. 5E) is a planar antenna with a circular exciting panel. The diameter of the panel is 25 mm, which is based on the calculated wavelength in soil using equation (11).

The elliptical antenna (FIG. 5F) size can be varied due to different operating frequencies. In this example, the operation frequency is 433 MHz, and as such, the antenna includes a rectangular ground panel that is 125 mm by 85 mm. The exciting panel is elliptical with two axes of 62 mm and 49 mm.

In the following examples, the antennas are buried at two depths (0.1 m and 0.3 m) and each antenna is connected to a 0.3 m coaxial cable. The antennas are buried horizontally with the exciting panel facing the soil-air interface. The other end of the cable is connected to a portable network analyzer that is employed to measure the return loss of each antenna. The two depths were selected based on information including typical sensor nodes in WUSN applications for agriculture are usually buried at 0.3 m depth to avoid the impacts from agriculture machinery and at these depths, the impact from the soil-air interface can be captured.

Effects of Burial Depth

The return losses for each of the antennas at different depths in soil are shown in FIG. 5A-5F. In addition, the return loss of the antennas in air is also depicted. The soil moisture in this measurement is 20%, which is also a normal condition for growing crops.

As shown in FIG. 5A, two resonant frequencies for the GSM antenna in air are 1.052 GHz and 1.921 GHz. However, when the antenna is buried in soil, the resonant frequencies shift to lower frequencies. For a burial depth of 10 cm, the resonant frequencies are 571.8 MHz and 1.442 GHz, respectively. When the burial depth is 30 cm, the corresponding resonant frequencies are 631.8 MHz and 1.502 GHz. This shift of resonant frequency is related to the change of the wavelength in soil. As is typical, the new resonant frequencies in soil cannot be calculated based solely on the corresponding wavelengths in soil due to the reflection from the soil-air interface.

When the antennas arc buried in soil, the shape of the return loss curve typically changes. This change can be seen in the 433 MHz antenna (FIG. 5B) and the original MicaZ antenna (FIG. 5D). In the 433 MHz antenna, multiple resonant frequencies 502 occur at lower frequencies when the antenna is buried in soil. In the MicaZ antenna case, when the antenna is buried, the return loss at the resonant frequency is 15 dB lower than the antenna placed in air, as shown at arrow 504. The reason is that the impact of the soil medium is not linear at different frequencies, as indicated in equations (10) and (12) above, where β is a linear function of $f$, but $Z_a$ is not a linear function of β. As shown in the figures, the impedance at the lower frequency range is impacted more than the higher frequency range. For the 433 MHz antenna (FIG. 5B), return loss at frequencies higher than 4 GHz remains similar to the results in air and for the MicaZ antenna (FIG. 6D), this is true for frequencies higher than 5 GHz. The results of the Mica2 antenna (FIG. 5C) indicate it has poor performance across the frequency range as the return losses of the resonant frequencies are higher than −10 dB.

Unlike the dipole antennas, the shapes of the return loss curves of the planar antennas in soil remain similar to that in air (FIGS. 5E and 5F). This may be due to the different radiating mechanism of the planar antenna, where the waves first propagate through the fringe of the substrate, which does not change when the antenna is buried in soil. The substrate can mitigate the impact of soil in the near field of the radiation. Thus, the return loss curve remains similar in air and soil for these planar antennas.

Figure 6A:
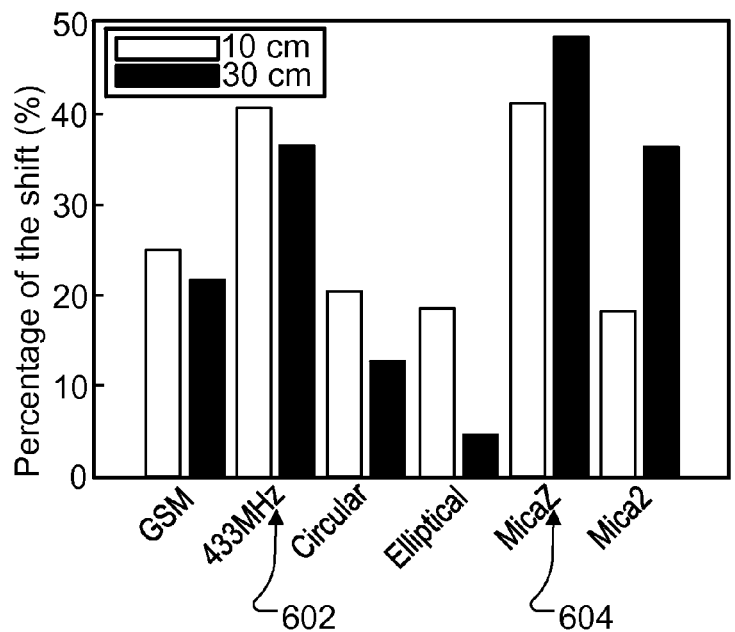
FIGS. 6A-B illustrate resonant frequency shifts for a number of different antennas placed in different mediums.

The specific shift in the resonant frequencies of each antenna is a known factor and the percentage of the shift compared to the resonant frequencies in air is shown in FIG. 6A. As shown in FIG. 6A, the percentage of the shift is not the same for different antennas. The 433 MHz antenna and the MicaZ antenna have the largest shift, as shown by arrows 602 and 604, respectively. For the MicaZ antenna, the shift is 42% when the burial depth is 10 cm and 48% when the burial depth increases to 30 cm. Meanwhile, for the 433 MHz antenna, the shift is 40% when the burial depth is 10 cm and 36% when the burial depth is 30 cm. The difference of the shift at different depths is typically caused by the reflected wave from the soil-air interface, which disturbs the current distribution on the antenna and hence the impedance of the antenna. This impact is not linear for different frequencies. Also, due to the phase of the reflected electric field, the shift fluctuates at different depths. In addition, this fluctuation is not the same for different antennas. For example, the elliptical planar antenna, the shift can be reduced from 19% to 5% if the burial depth is increased from 10 cm to 30 cm. On the other hand, for the Mica2 antenna, with the same change in the burial depth, the shift is increased from 18% to 36%. Therefore, for antennas in underground communications, the environment cannot be considered as homogeneous and the impact of the reflected waves for particular antennas can be analyzed to determine a precisely designed antenna for the soil. Moreover, this impact cannot be generalized and each different antenna type may require specific analysis.

Figure 6B:
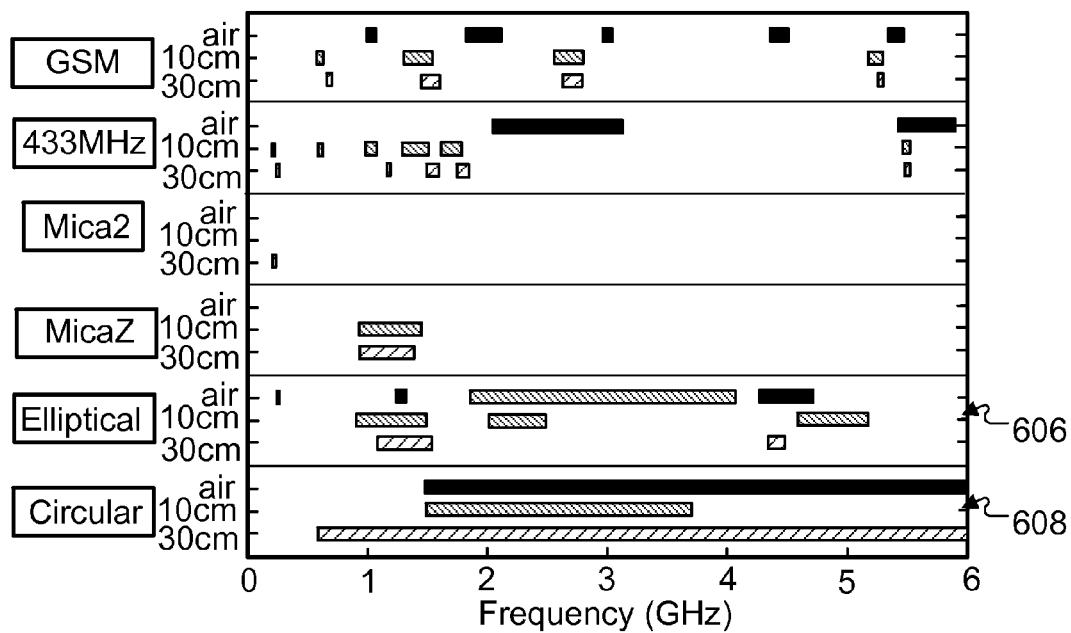

FIG. 6B illustrates a number of frequency bands of the above described antennas in different mediums. When designing antennas for underground use, the design should take into account the bandwidth effects in particular mediums. In practice, the return loss of −10 dB is typically employed as the threshold to define the frequency band of a particular antenna. The bandwidth measurements for the antennas described in FIGS. 5A-5F are shown in FIG. 6B. The blocks indicate the frequency bands of the antennas. As shown, the two planar antennas 606 and 608 have the widest bandwidths amongst the antennas. As an example, it can be observed that the circular planar antenna (FIG. 5E) has an extremely wide bandwidth of (0.54-6.0 GHz in 30 cm depth). This characteristic is desirable in the underground communication since it can accommodate different soil situations.

Effects of Soil Moisture

Soil moisture changes varied amounts over time since the natural precipitation process changes over time. The following examples show recordings for the return loss of four antennas (GSM antenna, 433 MHz antenna, and the two planar antennas) in three different soil moisture settings (i.e., dry (5% VWC), normal (20% VWC), and wet (37% VWC). The soil composition of the test bed is 23.7% of sand and 28.7% of clay.

Figure 7A:
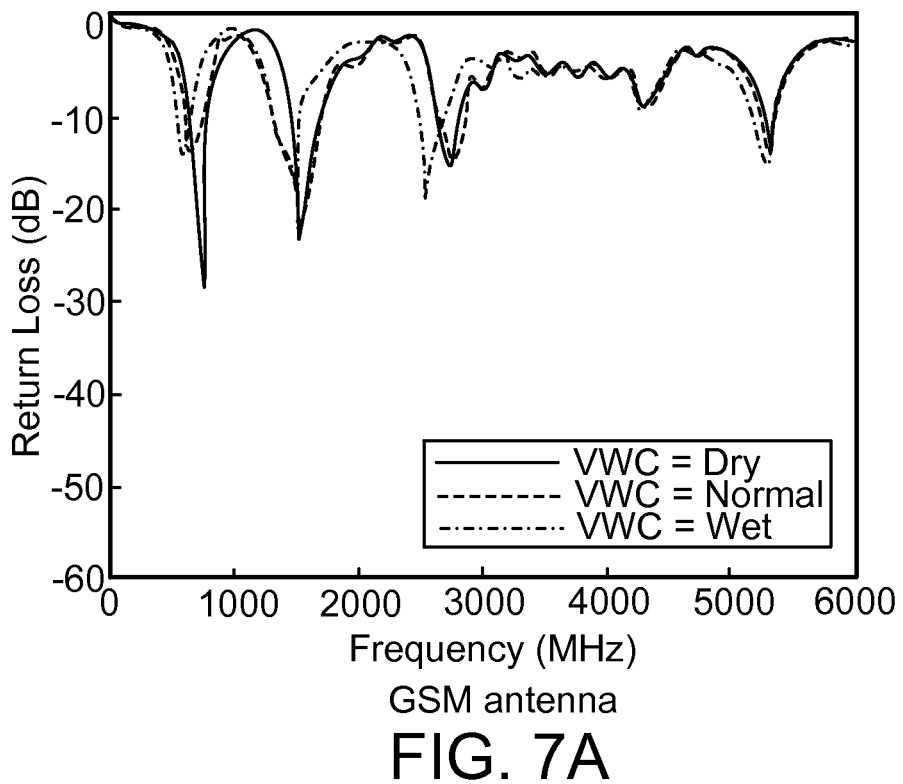
FIGS. 7A-7D illustrate measured return losses for a number of antennas buried at a depth of 30 centimeters.
Figure 7B:
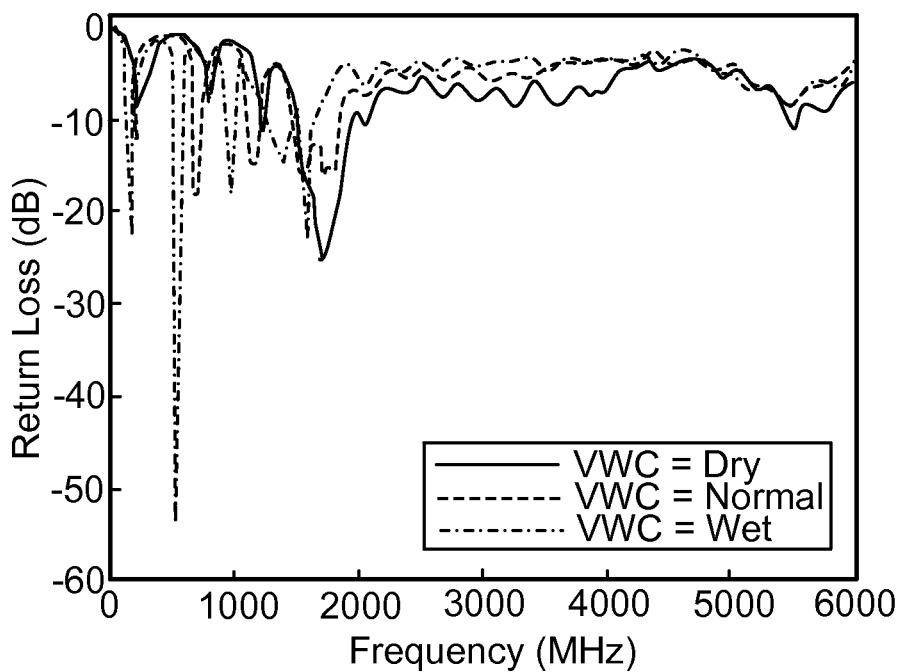

FIGS. 7A-7D illustrate measured return losses for a number of antennas buried at a depth of 30 centimeters. As described above in reference to equations (1) and (2), when soil moisture increases, the permittivity of the soil increases too, which causes the wavelength to further reduce. Therefore, in the return loss curves shown in FIGS. 7A and 7B, the resonant frequency shifts to an even lower range when the soil moisture increases. For the GSM antenna (FIG. 7A), when the volumetric water content (VWC) increases from 5% to 20%, the resonant frequency moves to a frequency 3% lower than the resonant frequency in air. Furthermore, when the VWC increases from 20% to 37%, an additional 3.1% decrease in the resonant frequency is observed. Moreover, the exact values of the return loss at the resonant frequency vary for different soil moisture values. The change in the return loss is considerable for the 433 MHz antenna (FIG. 7B). At a frequency of 272 MHz, for VWC=5%, the return loss at the resonant frequency is −8 dB. However, when VWC increases to 20%, this resonant frequency shifts to 242 MHz and the return loss reduces to −18 dB. With a further increase in VWC to 37%, the resonant frequency shifts to 182 MHz and the return loss is further reduced to −23.5 dB. The empirical results confirm that when an antenna is buried in soil, both the resonant frequency and the return loss value at that resonant frequency change. Thus, in the design of an antenna, even if it performs well in air, equivalent performance cannot be guaranteed when the same antenna is buried in soil.

Figure 7C:
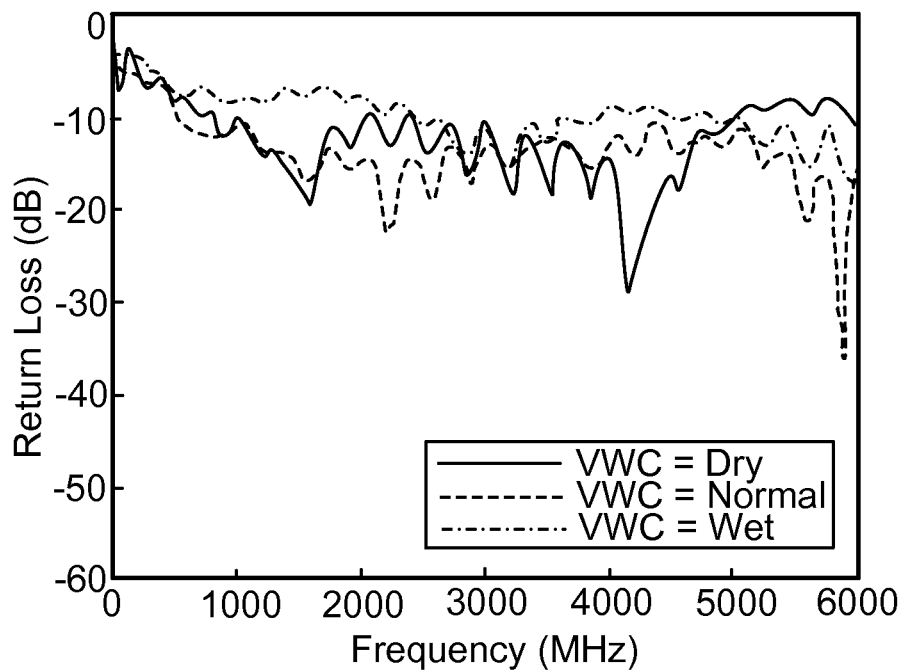
Figure 7D:
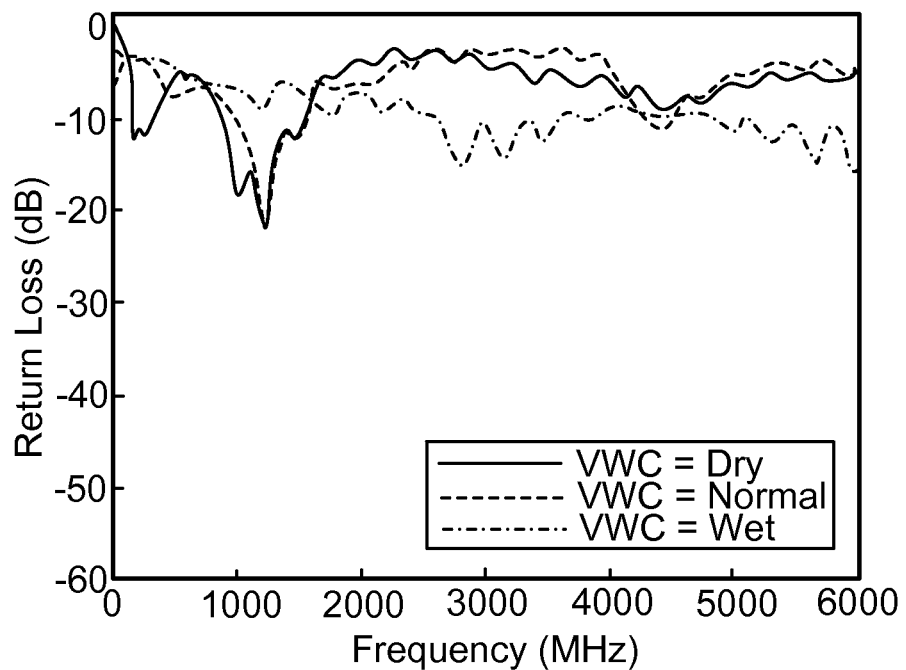

As for the two planar antennas measurements shown in FIGS. 7C and 7D, the shapes of the return loss curves change considerably over the change of the soil moisture. This may be partly caused by the lack of insulation for these two antennas. Thus, the change of water content directly impacts the current distribution of the antenna.

Figure 8:
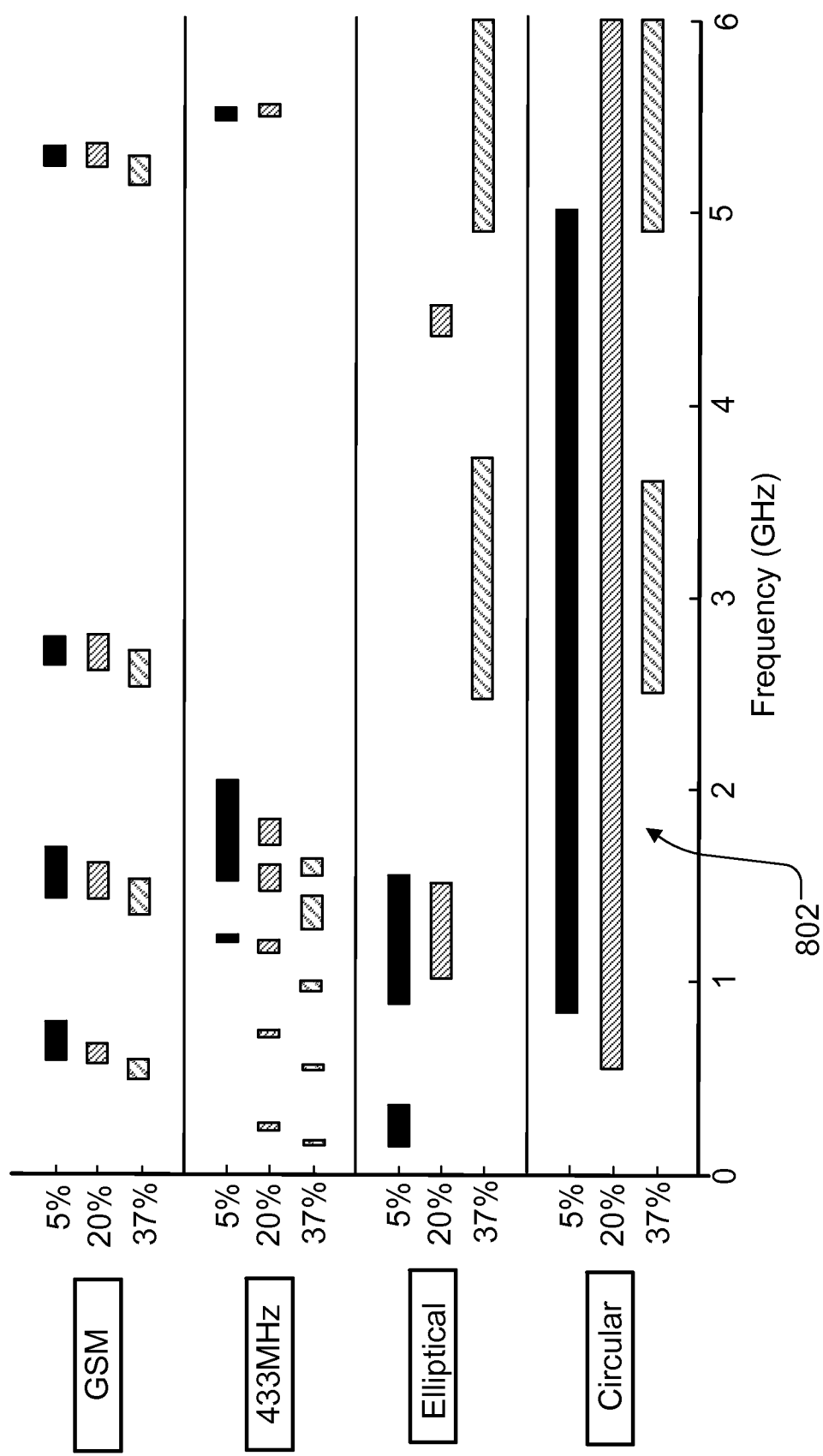
FIG. 8 illustrates a number of frequency bands for different antennas in different soil moisture.

FIG. 8 illustrates a number of frequency bands for different antennas in different soil moisture. The frequency bands for the three soil moisture values are indicated by blocks for the GSM antenna, the 433 MHz antenna, the elliptical antenna, and the circular planar antenna. It is observed that the circular planar antenna 802 has a wide band in the different soil moisture values. The return loss is less than −10 dB for a frequency range of 2.4 GHz-3.6 GHz and 4.8 GHz-6 GHz for all the three soil moisture values. This trait can be used to design antennas for WUSNs since it means the performance of the antenna will be maintained even if the soil moisture varies.

Example Wide Band Antenna: Underground Circular Antenna Design

In general, the realization of wireless underground sensor networks (WUSNs) relies on the establishment of reliable communication links, where the antenna design becomes an important factor due to the significant impacts of soil in which sensors are buried. The following example describes an example wide band antenna designed for an agricultural WUSN application. Empirical evaluations are illustrated above to show that an antenna designed considering both the change in wavelength in soil and the reflection from the soil-air interface can accommodate major changes in soil moisture and improve communication distances by up to 587% compared to antennas that are designed based on only the wavelength change in soil.

Figure 9:
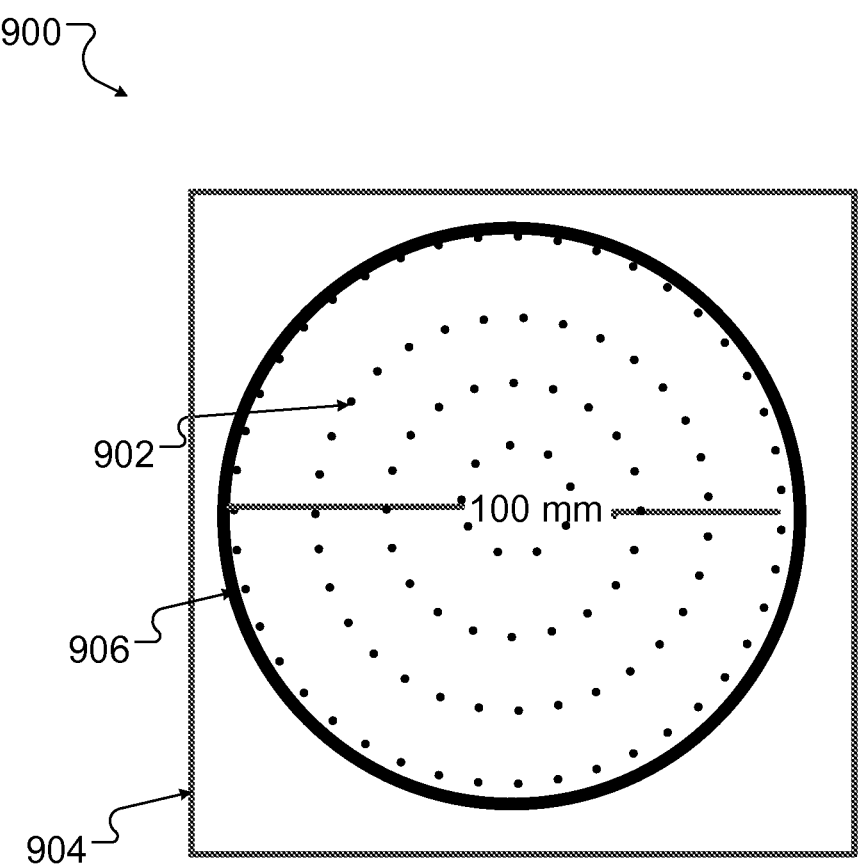
FIG. 9 is an example diagram of a circular planar antenna for use in wireless underground sensor networks.

FIG. 9 is an example of a circular planar antenna structure 900 for use in a wireless underground sensor network. The antenna 900 can be designed to accommodate major changes in soil moisture and can include a plurality of configurations of sensors, arrays, sub-arrays, and filters. In some implementations, an antenna with a resonant frequency of 433 MHz may provide characteristics that offer minimal attenuation and minimal antenna size. As such, a number of commercial chips for this industrial, scientific, and medical (ISM) band are available and can be readily used in commodity sensor motes.

In one example, the antenna 900 is an underground circular planar antenna for radiating through a dissipative medium, such as soil. The antenna 900 shown here has a diameter of 100 mm, but other diameters are possible. The substrate of the antenna 900 may be FR-4 material with a thickness of 1.6 mm, for example. The feed line of antenna 900 may be a coplanar waveguide structure, as shown at 906. In some implementations, the circular planar antenna 900 includes one or more microwave transmission plates, susceptors, radiation holes, electrical conductors, and/or other components that provide particular radiation patterns and functionality for underground antennas. As shown, the antenna 900 includes a number of electrical conductors 902 formed through a dielectric substrate 904. The coplanar waveguide structure 906 is shown disposed on the substrate 904 as well.

The electrical conductors 902 can, for example, be oriented and the antenna structure 900 can be buried within a dissipative medium, such as soil. For example, the structure 900 may be buried in the dissipative medium at about 0.1 meters up to about 1.0 meter. The electrical conductors may be adapted to radiate signals at a frequency in a half-space adjacent to the dissipative medium. For example, a beamwidth state can be configured for one or more of the electrical conductors based at least in part on the relative permittivity of the dissipative medium.

The electrical conductors 902 can be arrayed or arranged in a predetermined pattern. For example, the intervals may be set to half a wavelength, a quarter wavelength, or a full wavelength. In some implementations, the conductors 902 may form another shape, such as a t-shape or an arch shape, for example. The array pattern formed by conductors 902 is not limited to a specific one, and as such, it may be spiral or radial other than concentric.

In some implementations, the one or more electrical conductors are oriented toward and substantially parallel to an interface between free space and the dissipative medium. This orientation can provide a radiation pattern that is unidirectional towards the interface.

In some implementations, the antenna 900 includes a conductive surface facing the substrate 904. The conductive surface may be adapted to concentrate a substantial portion of energy radiated by the one or more electrical conductors in the half-space adjacent to the dissipative medium.

In some implementations, the antenna 900 circuitry adaptable to provide a beamwidth that accommodates the critical angel of the incidence ($\theta_c$) of different soil conditions, which is between about 5 degrees and about 15 degrees. In some implementations, the antenna 900 is designed as a stand-alone component and is not tunable. That is, the antenna 900 can be designed such that it operates in a wide band of frequencies without requiring tuning to particular impedance changes.

Figure 10:
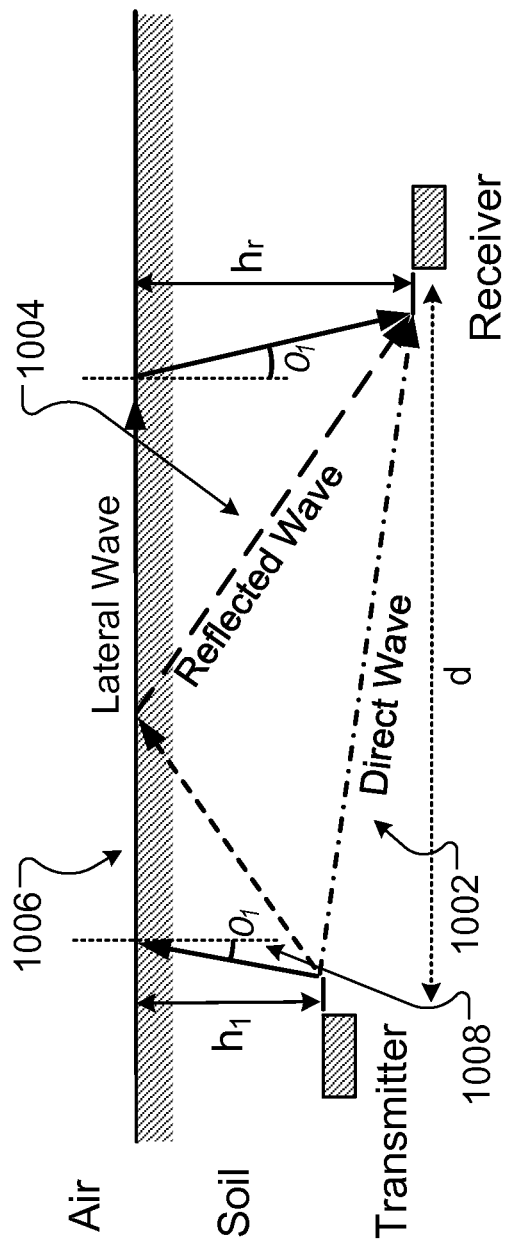
FIG. 10 illustrates an example of three paths of subsurface underground communication.

FIG. 10 illustrates an example of three paths of subsurface underground communication. In operation, the circular planar antenna 900 provides a wide signal bandwidth as well as a highly desirable radiation pattern. In particular, in underground communications at the depth range of 0.3-1.0 m, three paths can be modeled and/or measured a direct wave 1002, a reflected wave 1004, and a lateral wave 1006, as shown in FIG. 10. Of the three paths, the lateral wave 1006 is typically dominant in the far field because the attenuation in air is much smaller than the attenuation in soil. Therefore, the radiation pattern of the antenna buried in soil should have a radiation pattern such that the lateral wave is maximized. As shown, the lateral wave 1006 occurs when the incident wave is at a critical angle 1008 ($\theta_c$). The critical angle 1008 represents the angle above which no refraction exists.

The critical angle 1008 is a function of soil permittivity, which is a function of soil moisture. Hence, the critical angle 1008, ($\theta_c$), varies with the change in soil moisture. Due to the fact that the relative permittivity of soil is ten to one hundred times higher than air, the critical angle 1008 is typically less than 15 degrees in all soil moisture settings.

Based on the above analysis, a desired radiation pattern for the circular planar underground antenna 900 is unidirectional towards the soil-air interface. The beam width of the antenna 900 generally covers all critical angles in different soil moisture values, which are typically in the range of 5 to 15 degrees. Thus, the planar antennas have desirable radiation patterns when they are placed parallel to the soil-air interface.

Figure 11:
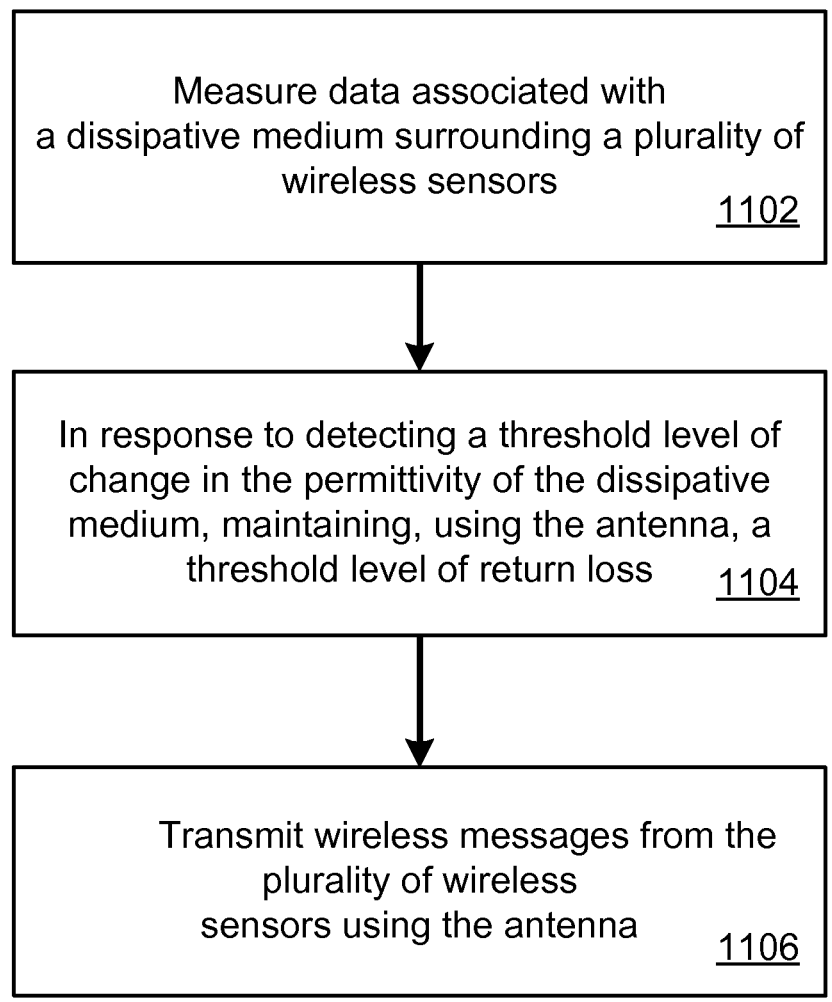
FIG. 11 is an example method for operating an underground antenna structure radiating through a dissipative medium.

FIG. 11 is an example method 1100 for operating an underground antenna structure radiating through a dissipative medium. In short, process 1100 determines real time characteristics (such as moisture level) from a dissipative medium (such as soil) and uses one or more sensors and/or antennas in order to ensure proper communication functionality is maintained. In general, the process 1100 can be performed by a sensor, processor, controller, or computer system capable of analyzing mediums and wirelessly communicating results to another system or network.

The process 1100 may begin with one or more wireless sensors measuring (1102) data associated with a dissipative medium surrounding a plurality of wireless sensors. The plurality of wireless sensors are coupled to an antenna structure and can collect the measured data and transmit such data to a network or server, such as network 104, and/or server 106. In some implementations, the plurality of wireless sensors can collect data from a number of depths within the dissipative medium. For example, the sensors can measure/collect data from about 0.1 meters below the surface of the dissipative medium up to and including about 1.0 meters below the surface of the dissipative medium.

At some point, the permittivity (i.e., moisture content or other characteristic) may change. In response to detecting a threshold level of change in the permittivity of the dissipative medium, the antenna can maintain (1104) a particular level of return loss. That is, the designed antenna maintains low return loss (e.g., less than −10 decibels) at the operation frequency. Maintaining or improving this level of return loss can ensure that wireless communications occur reliably and without interruption. In one example, the threshold level of change in the permittivity of the dissipative medium may be characterized by a five percent increase or decrease in the moisture level of the dissipative medium. In some implementations, the antenna results in a wireless communication distance increase for communications between the underground antenna structure and one or more other structures or networks. At some time, the sensors can transmit (or be polled to transmit) (1106) one or more wireless messages corresponding to the measured data from the plurality of wireless sensors using the wide-band antenna.

Figure 12:
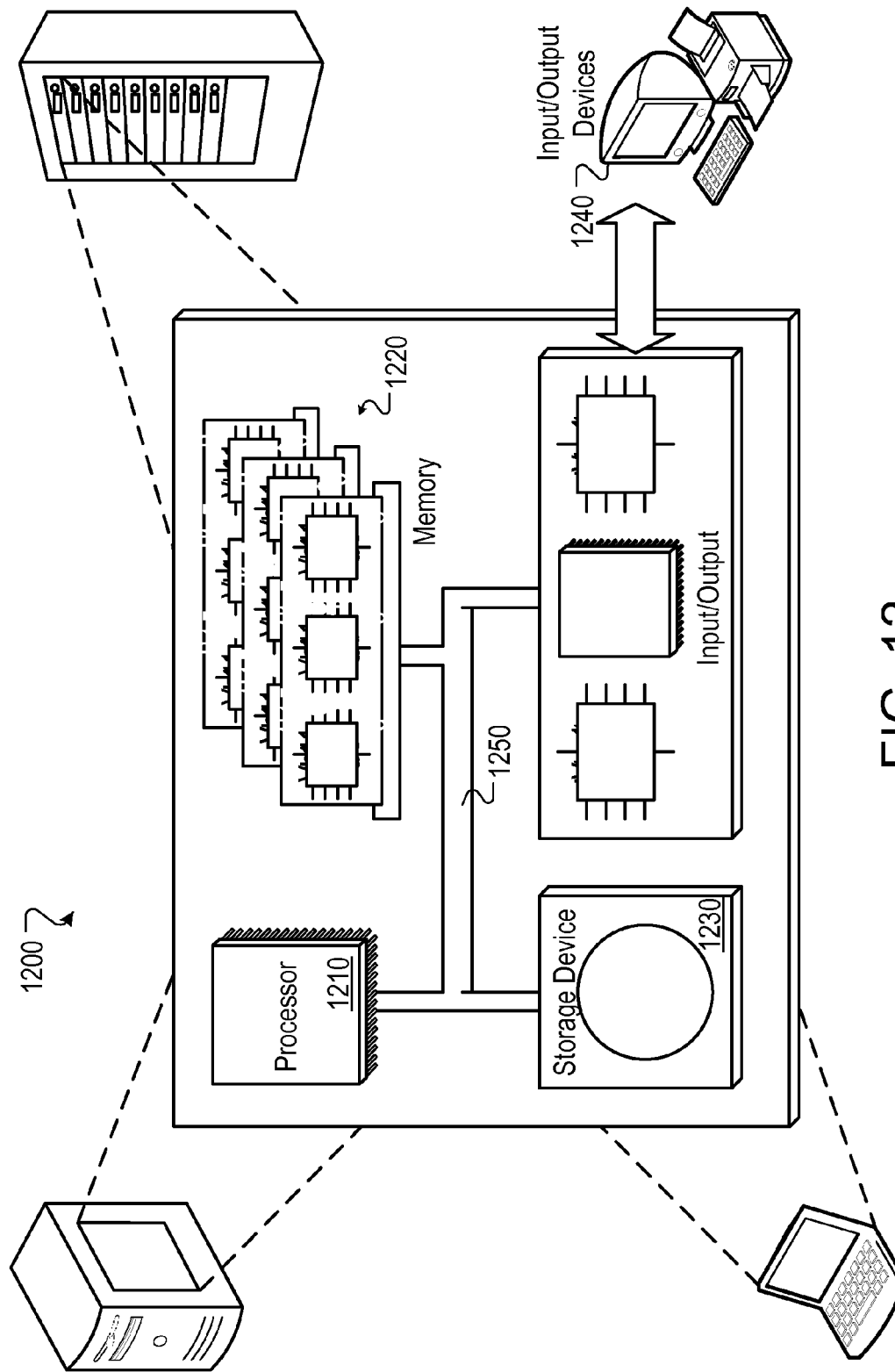
FIG. 12 is a block diagram of computing devices that may be used to implement the systems and methods described in this document.

FIG. 12 is a schematic diagram of a computing system 1200. The generic computing system 1200 can be used for the operations described in association with any of the computer-implemented methods or systems described previously, according to one implementation. The generic computing system 1200 includes a processor 1210, a memory 1220, a storage device 1230, and an input/output device 1240. Each of the processor 1210, the memory 1220, the storage device 1230, and the input/output device 1240 are interconnected using a system bus 1250. The processor 1210 is capable of processing instructions for execution within the generic computing system 1200. In one implementation, the processor 1210 is a single-threaded processor. In another implementation, the processor 1210 is a multi-threaded processor. The processor 1210 is capable of processing instructions stored in the memory 1220 or on the storage device 1230 to display graphical information for a user interface on the input/output device 1240.

The memory 1220 stores information within the generic computing system 1200. In one implementation, the memory 1220 is a computer-readable medium. In one implementation, the memory 1220 is a volatile memory unit. In another implementation, the memory 1220 is a non-volatile memory unit.

The storage device 1230 is capable of providing mass storage for the generic computing system 1200. In one implementation, the storage device 1230 is a computer-readable medium. In various different implementations, the storage device 1230 may be a floppy disk device, a hard disk device, an optical disk device, or a tape device.

The input/output device 1240 provides input/output operations for the generic computing system 1200. In one implementation, the input/output device 1240 includes a keyboard and/or pointing device. In another implementation, the input/output device 1240 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device or in a propagated signal, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; cloud-based memory devices and disks, magnetic disks such as internal hard disks and removable disks; magneto-optical disks; and CD-ROM and DVD-ROM disks. The processor and the memory can be supplemented by, or incorporated in, ASICs (application-specific integrated circuits).

In some implementations, system 1200 may be a communication system that can be implemented in one or more sensors or mobile devices described above. The system 1200 can be adapted to communicate wirelessly to and from itself. For example, the system 1200 receives and transmits information wirelessly using a transceiver (not shown), with the received signals being passed to a signal processor (not shown). The signal processor can include digital signal processing (DSP) circuitry for processing the received signals.

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A computer program (also known as a program, software, software application, script, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of embodiments of the invention have been described. Nevertheless, it will be understood that various modifications may be made without departing from the spirit and scope of the invention. For example, various forms of the flows shown above may be used, with steps re-ordered, added, or removed. Also, although several applications of search queries and methods to obtain useful query results have been described, it should be recognized that numerous other applications are contemplated. Accordingly, other embodiments are within the scope of the following claims.

What is claimed is:

1. An underground antenna structure for radiating through a dissipative medium, the antenna structure comprising:
    a dielectric substrate;
    a feeding structure disposed on the substrate; and
    one or more electrical conductors disposed on the substrate, oriented, and buried within the dissipative medium, the electrical conductors adapted to radiate signals at a frequency in a half-space adjacent to the dissipative medium, the adaptation comprising a beamwidth state for one or more of the electrical conductors based at least in part on the relative permittivity of the dissipative medium.

2. The structure of claim 1, wherein the antenna structure comprises a wide band antenna that maintains a return loss of less than about minus 10 decibels for a plurality of soil conditions.

3. The structure of claim 1, wherein the beamwidth state results in a wireless communication distance increase for communications between the underground antenna structure and one or more other structures or networks.

4. The structure of claim 1, wherein the one or more electrical conductors are oriented toward and substantially parallel to an interface between free space and the dissipative medium and the corresponding radiation pattern emitted by the underground antenna structure is unidirectional towards the interface.

5. The structure of claim 1, further comprising circuitry adaptable to provide a beamwidth that accommodates a critical angle of incidence from soil to air at different soil conditions.

6. The structure of claim 1, wherein the dissipative medium comprises non-homogenous soil.

7. The structure of claim 1, wherein the antenna structure is buried in the dissipative medium at about 0.1 meters up to about 1.0 meter.

8. The structure of claim 2, wherein the diameter of the wide band antenna is about 100 millimeters.

9. The structure of claim 5, wherein the critical angle of incidence comprises a critical operating angle $\theta_c$ that is between about 5 degrees and about 15 degrees, wherein the critical operating angle $\theta_c$ value is based at least in part on the permittivity of the dissipative medium, and wherein the critical operating angle $\theta_c$ represents the angle above which no refraction exists for the antenna structure.

10. A wireless underground system for measuring conditions in a dissipative medium comprising:

one or more wireless moisture sensors, each including a sensor board, a processor within the sensor board, and a transceiver in communication with the processor and coupled to an antenna;

a gateway configured to receive and transmit wireless messages and further configured to communicate with a network and to receive and relay wireless messages from the one or more wireless moisture sensors; and wherein each of the wireless moisture sensors are configured to (i) collect data about the conditions of the dissipative medium from the plurality of sensors along a length of the dissipative medium, and (ii) in response to detecting a threshold level of change in the permittivity of the dissipative medium, maintain a threshold level of return loss.

11. The system of claim 10, wherein the threshold level of change in the permittivity of the dissipative medium comprises an increase or decrease in the moisture level of the dissipative medium of about 5 percent and the threshold level of return loss is less than about minus 10 decibels.

12. The system of claim 10, wherein the one or more wireless moisture sensors collect data from at least two depths within the dissipative medium.

13. The system of claim 10, wherein the dissipative medium is non-homogenous soil.

14. The system of claim 12, wherein the at least two depths comprise about 0.1 meters below the surface of the dissipative medium and about 1.0 meters below the surface of the dissipative medium.

15. A method for operating an underground antenna structure radiating through a dissipative medium, the method comprising:

measuring, using the underground antenna structure, data associated with the dissipative medium surrounding a plurality of wireless sensors, wherein the plurality of wireless sensors are coupled to the antenna structure;

in response to detecting a threshold level of change in the permittivity of the dissipative medium, maintaining a threshold level of return loss, for the antenna structure, of less than about minus 10 decibels; and transmitting one or more wireless messages from the plurality of wireless sensors using the antenna, the messages corresponding to the measured data.

16. The method of claim 15, wherein the threshold level of change in the permittivity of the dissipative medium comprises an increase or decrease in the moisture level of the dissipative medium of about 5 percent.

17. The method of claim 15, wherein the plurality of wireless sensors collect data from at least two depths within the dissipative medium.

18. The method of claim 15, wherein the dissipative medium is non-homogenous soil.

19. The method of claim 17, wherein the at least two depths comprise about 0.1 meters below the surface of the dissipative medium and about 1.0 meter below the surface of the dissipative medium.

* * * * *